United States Patent
Galas et al.

(10) Patent No.: US 8,828,963 B2
(45) Date of Patent: Sep. 9, 2014

(54) DIAGNOSIS AND TREATMENT OF CHRONIC LYMPHOCYTIC LEUKEMIA (CLL)

(75) Inventors: David Galas, Seattle, WA (US); Kai Wang, Bellevue, WA (US); Guy Berchem, Luxembourg (LU); Etienne Moussay, Luxembourg (LU)

(73) Assignees: Institute for Systems Biology, Seattle, WA (US); Centre de Recherche Public de la Sante, Luxembourg (LU)

( * ) Notice: Subject to any disclaimer, the term of this patent is extended or adjusted under 35 U.S.C. 154(b) by 175 days.

(21) Appl. No.: 13/423,129

(22) Filed: Mar. 16, 2012

(65) Prior Publication Data

US 2012/0252871 A1  Oct. 4, 2012

Related U.S. Application Data

(60) Provisional application No. 61/454,464, filed on Mar. 18, 2011.

(51) Int. Cl.
*C12N 15/113* (2010.01)
*A61K 48/00* (2006.01)
*C12Q 1/68* (2006.01)

(52) U.S. Cl.
CPC ........ *C12Q 1/6886* (2013.01); *C12Q 2600/178* (2013.01)
USPC ..................... 514/44 A; 514/44 R

(58) Field of Classification Search
None
See application file for complete search history.

(56) References Cited

PUBLICATIONS

Bichi et al., "Human Chronic Lymphocytic Leukemia Modeled in Mouse by Targeted TCL1 Expression," Proc. Natl. Acad. Sci. USA (2002) 99(10):6955-6960.
Binet et al., "Investigation of a New Parameter in Chronic Lymphocytic Leukemia: the Percentage of Large Peripheral Lymphocytes Determined by the Hemalog D. Prognostic Significance," Am J. Med. (1977) 63(5):683-688.
Calin et al., "A MicroRNA Signature Associated with Prognosis and Progression in Chronic Lymphocytic Leukemia," N. Engl. J. Med. (2005) 353(17):1793-1801.
Calin et al., "MicroRNA Profiling Reveals Distinct Signatures in B Cell Chronic Lymphocytic Leukemias," Proc. Nat. Acad. Sci. (2004) 101(32):11755-11760.
Cimmino et al., "miR-15 and miR-16 Induce Apoptosis by Targeting BCL2," Proc. Natl. Acad. Sci. USA (2005) 102(39):13944-13949.
Cortez et al., "MicroRNA Identification in Plasma and Serum: a New Tool to Diagnose and Monitor Diseases," Expert Opin. Biol. Ther. (2009) 9(6):703-711 Abstract only.
Cuesta et al., "miR-181a Regulates Cap-Dependent Translation of p27(kip1) mRNA in Myeloid Cells," Mol. Cell Biol. (2009) 29(10):2841-2851.
De Totero et al., "The Opposite Effects of IL-15 and IL-21 on CLL B Cells Correlate with Differential Activation of the JAK/STATand ERK1/2 Pathways," Blood (2008) 111(2):517-524.
Fulci et al., "Quantitative Technologies Establish a Novel MicroRNA Profile of Chronic Lymphocytic Leukemia," Blood (2007) 109(11):4944-4951.
Galardi et al., "miR-221 and miR-222 Expression Affects the Proliferation Potential of Human Prostate Carcinoma Cell Lines by Targeting p27Kip1," J. Biol. Chem. (2007) 282(32):23716-23724.
Haferlach et al., "Comprehensive Genetic Characterization of CLL: a Study on 506 Cases Analysed with Chromosome Banding Analysis, Interphase FISH, IgV(h) Status and Immunophenotyping," Leukemia (2007) 21(12):2442-2451.
International Search Report and Written Opinion for International Application No. PCT/US2012/029557, mailed Aug. 24, 2012, 11 pages.
Kay et al., "Prognostic Factors in Chronic Lymphocytic Leukemia," Curr. Hematol. Malig. Rep. (2007) 2(1):49-55.
Kitada et al., "Expression of Apoptosis-Regulating Proteins in Chronic Lymphocytic Leukemia: Correlations with In Vitro and In Vivo Chemoresponses," Blood (1998) 91(9):3379-3389.
Klein et al., The DLEU2/miR-15a/16-1 Cluster Controls B Cell Proliferation and its Deletion Leads to Chronic Lymphocytic Leukemia,: Cancer Cell. (2010) 17(1):28-40.
McManus, "MicroRNAs and Cancer," Semin. Cancer Biol. (2003) 13(4):253-258.
Pallasch et al., "miRNA Deregulation by Epigenetic Silencing Disrupts Suppression of the Oncogene PLAG1 in Chronic Lymphocytic Leukemia," Blood (2009) 114(15):3255-3264.
Rai et al., "Clinical Staging of Chronic Lymphocytic Leukemia," Blood (1975) 46(2):219-234.
Redondo-Munoz et al., "Matrix Metalloproteinase-9 is Up-Regulated by CCL21/CCR7 Interaction via Extracellular Signal-Regulated Kinase-1/2 Signaling and is Involved in CCL21-Driven B-Cell Chronic Lymphocytic Leukemia Cell Invasion and Migration," Blood (2008) 111(1):383-386.
Stamatopoulos et al., "MicroRNA-29c and MicroRNA-223 Downregulation has In Vivo Significance in Chronic Lymphocytic Leukemia and Improves Disease Risk Stratification," Blood (2009), 113: 5237.
Stamatopoulos et al., "Quantification of ZAP-70 mRNA in B Cells by Real-Time PCR is a Powerful Prognostic Factor in Chronic Lymphocytic Leukemia," Clin. Chem. (2007) 53(10):1757-1766.
Tsujiura et al., "Circulating MicroRNAs in Plasma of Patients with Gastric Cancers," Br. J. Cancer (2010) 102(7):1174-1179.
Vrhovac et al., "Prognostic Significance of the Cell Cycle Inhibitor p27Kip1 in Chronic B-Cell Lymphocytic Leukemia," Blood (1998) 91(12):4694-4700.
Wang et al., "Circulating MicroRNAs, Potential Biomarkers for Drug-Induced Liver Injury," Proc. Natl. Acad. Sci. USA (2009) 106(11):4402-4407.

*Primary Examiner* — James Martinell
(74) *Attorney, Agent, or Firm* — Morrison & Foerster LLP

(57) ABSTRACT

New markers in the form of miRNA levels in plasma are provided for indicating the presence of CLL in a subject as well as suggesting routes of therapeutic treatment.

4 Claims, 12 Drawing Sheets

$GCNF_01   [TCAAGTCAAG-TCA]

ZAP-70 promoter region (-651 to +299)

```
GCGACTGAGAGACAGCTAGTGC[TT]A[AT]AATTCTCTCAGCCCCAAAGAAGGGCTTGATTTCTTTATACTTTGGTT
TAGAAAGGACAGGTGGGGTCTAAACAATCTTACAGAAGTCAGGCAAAAAGTTAAAGGATAAATGGTTACGGG
AAAGCAAACAGTTCCAGGTGCAGGGCTTAAAATCTATCAAGGTGATAGACACGGGCTTTGGCGTTA[AGAGC]CGG
ACACAAACGCCGGGCTCTGGGGCTTCTTTGGATGTGTGGGAGTCCTGTGCTCTCTTAGCTCGGGATATCTTA
TCAGTTAATTGCATTTGCAAGATGGAAGCCAAGATGGAGTCTGTCTGGCTCTCTTAGCTAGGGA[AGT]T[AT][AT]GT[T]AAAACAAGGTAG
CTGCAAATGAAAGAGCCACTTAACAACAAGGGCAGCAGACCCCAAGAGAAGAAAGTTTAGAGTCTCCAAGAGTCGGCCCAGGGC
GGTATCACAACAGTCTCTTAACAACAGTGTCCTGAGGCCCCACAGAGCCTTGGGCACTAGAGGCTGTGACGACTGAGCGAGGAGTT
AGTTCCACACAGTCTCTTCCTCCCAGAGTGTGCCACAGGGCCTTGGGCACTAGAGGCCGAGGGGTGCTCTGCAGGCCCTCTCT
GTGCAAGGGCATGAGGTGTGGCCACAGCGGGGATGGACCTCAGCCAGGTTCAGTCTCGTGGGAAAGGTCCCAGTTGGGCCGGCTAGC
GAGGAGGTGTGGCCACAGCGGGGATGGACCTCAGCCAGGTTCAGTCTCGTGGGAAAGGTCCCAGTGGGCCGGCTAGC
ACTGGGAGTCCCTGGCTCTGTGTCTGGGACACACAGTGCCCAGGCTTCCGGCCTCCTCCAGCCTGG
CTTGGGGATACCCTGGGACACACAGTGCCCAGGCTTCCGGCCTCCTCCAGCCCTGG
```

Binding matrix

| | A | C | G | T | | Consensus |
|---|---|---|---|---|---|---|
| A | 9 | 15 | 8 | 5 | | N |
| C | 2 | 5 | 7 | 23 | | T |
| G | 3 | 28 | 5 | 1 | | C |
| T | 31 | 1 | 4 | 1 | | A |
| | 1 | 0 | 36 | 0 | | [G] |
| | 0 | 0 | 13 | 23 | | K |
| | 0 | 0 | 0 | 37 | | [T] |
| | 0 | 37 | 0 | 0 | | [C] |
| | 37 | 0 | 0 | 0 | | [A] |
| | 36 | 1 | 0 | 0 | | A |
| | 0 | 1 | 34 | 3 | | G |
| | 0 | 1 | 17 | [18] | | K |
| | 1 | 1 | 2 | 33 | | [T] |
| | 0 | 35 | 0 | 2 | | [C] |
| | 34 | 1 | 1 | 1 | | [A] |
| | 9 | 14 | [6] | 8 | | N |
| | 6 | 14 | [7] | 10 | | N |

FIG. 8

```
                        SEQUENCE LISTING

<160> NUMBER OF SEQ ID NOS: 1

<210> SEQ ID NO 1
<211> LENGTH: 1000
<212> TYPE: DNA
<213> ORGANISM: Homo sapiens
<220> FEATURE:
<221> NAME/KEY: misc_feature
<223> OTHER INFORMATION: promoter region of ZAP-70 gene

<400> SEQUENCE: 1
gcgactgaga gacagctagt gctcaaaatt ctctcagccc caaagaaggg gcttgatttt      60
cttttatact ttggtttaga aaggacaggt gggggtctaa aacaatctta cagaagtaaa     120
gcaggcaaaa agttaaaagg ataaatggtt acgggaaagc aaacagttcc aggtgcaggg     180
gcttaaaatc tatcacaagg tgatagacac ggggctttgg gcgttatcaa ccggacacaa     240 acgccgggggc tctgggtgct attaaccggg cgaattcctg ggaactgcgg atatagcttg     300
ccacagtatc ttatcagtta attgcattct tggatgtgct gggagtcagc ttgcacaaat     360
taagtccttg aggaagcggg gtgggtaagg ggctgcaaat gaaagagcca agatggagtc     420
tgtctggctc tcttagctaa gggagagtca attcaggtta aaacaaggta gggtatcaca     480
agcccactta acaagggcag caggacccca agaagaaaag ctttaggagt ctccacagtg     540
ggcccagggc agttccacac aggtctctga ggccccacag acaggagagc tgtgacgact     600
cccttagtgc ccaagaaagc aaggaggtgg tgggcaaggg gctcccagag gccttggggc     660
actagagggg agatggagcc gagggagtgg ctctgcaggc ccctctctga gagagtgcat     720
gaggtgtggc cccaggccca agggtagggg gtgcacaggg tgagggaagg gaggagagga     780
agaggaggag gaggtggtgg ccacagcggg atggcactca gccaggttca gcttcgtggg     840
aaaggtccca ggtgggccgg gctagcactg gggatgccct ggctctgtgt ctcggttggg     900
tggctgactc ctcctggaac gcatccctga catcctccag gctggcttgg ggatactctg     960
gggacacaca gtgcccaggc ttccggcctc ccagccctgg                          1000
```

DIAGNOSIS AND TREATMENT OF CHRONIC LYMPHOCYTIC LEUKEMIA (CLL)

CROSS-REFERENCE TO RELATED APPLICATION

This application claims priority to U.S. provisional application 61/454,464 filed 18 Mar. 2011. The contents of this document are incorporated herein by reference in their entirety.

REFERENCE TO SEQUENCE LISTING SUBMITTED VIA EFS WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 655652003800Seqlist.txt | May 22, 2012 | 1,698 bytes |

TECHNICAL FIELD

The invention relates to markers for incidence of CLL and implication of these markers for treatment.

BACKGROUND ART

Chronic lymphocytic leukemia (CLL) is the most common hematologic disease affecting adults in Western countries. Although CLL remains an incurable disorder, early stage detection and treatment can control disease progression, while late stage patients are often unresponsive to treatments. The abnormal expressions of certain T cell markers by CLL B cells, such as ZAP-70, have been used in the stratification of the disease, i.e., overall survival is significantly worse in ZAP-70 positive cases. Like many other cancers, the diagnosis of the disease is often delayed due to the lack of symptoms in early stages.

Early cancer detection and disease stratification or classification are critical to successful treatment. Accessible, reliable, and informative cancer biomarkers can be medically valuable and could provide some relevant insights for cancer biology. Recent studies have suggested some improvements in detecting malignancies by the use of specific extracellular microRNAs (miRNAs) in plasma. In chronic lymphocytic leukemia (CLL), an incurable hematologic disorder, sensitive, early, and non-invasive diagnosis and better disease classification would be very useful for more effective therapies. These circulating, small non-coding RNA could be sensitive biomarkers for the early stages detection of the disease. We show here that certain miRNAs are present in CLL patient plasma at levels significantly different from healthy controls and from patients affected by other hematologic malignancies. The levels of several of these plasma miRNAs also have shown significant differences between zeta-associated protein 70 (ZAP-70) positive and ZAP-70 negative CLLs. Based on MicroRNA and mRNA expression data, we have identified a putative regulatory network associated with BCL2 and ZAP-70 expression in CLL. This result suggests both the possibility of using the levels of specific miRNAs in plasma to detect early CLL, to determine the ZAP-70 status, and also suggests potential therapeutic approaches that could be combined with already established clinical parameters.

DISCLOSURE OF THE INVENTION

The invention provides a convenient method to assess whether or not a particular subject is afflicted with CLL as well as to ascertain certain parameters associated with the severity or aggressiveness of this condition, such as whether the cells are ZAP-70 positive or negative and the stage of development of the condition. The subjects may be human, but may also be other vertebrate subjects, including laboratory models such as mice, rats, rabbits and the like. In one aspect, the invention method resides in measuring levels of miRNA in bodily fluids, such as blood, serum or plasma or other fraction of such fluids that contains miRNA. It has been shown that the levels or miRNA of various types differs among subjects who are afflicted with CLL and among subjects with various parameters characterizing their diseases. These diagnostic markers are shown below.

The miRNA levels can be assessed using art-known methods, and any suitable number may be employed. For example, a spectrum of miRNA of anywhere from 1 to 20, or more, miRNA molecules can be used as a pattern to diagnose the condition or its parameters. It may be advantageous to ascertain clusters of miRNA that show differences of expression in a consistent way among stages of disease or in respect to ZAP-70 positive/negative assessments. Alternatively, only a single miRNA may be sufficient to be diagnostic.

In another aspect, the invention is directed to methods of treating CLL based on the analysis set forth below. The need for therapies effective against CLL is evident. One possible mode which is part of the invention is to inhibit the production of ZAP-70 by downregulating the production of NR6A1 using any downregulatory method available in the art, including interfering RNA, antisense technology and the like. As shown below, miRNA's associated with NR6A1 are downregulated in CLL cells thus allowing production of NR6A1 at higher level, and thus higher levels of production of ZAP-70. By counteracting this effect of the normally present miRNA by interfering with expression of the gene NR6A1, the subject's CLL will be modified to a less aggressive form normally associated with ZAP-70 negative CLL.

We conducted a study to explore the changes of extracellular miRNA spectra in blood among CLL patient samples to provide a more accurate assessment of the disease, and improve the detection and classification of CLL. Based on the results, specific miRNA signatures associated with different CLL stages and ZAP-70 expression status have been obtained as shown in Table 1.

TABLE 1

List of differentially expressed miRNAs between the ZAP-70 positive and ZAP-70 negative samples. The miRNAs with higher levels in ZAP-70 positive plasma are those below the line.

| | | ZAP-70 Negative | | | ZAP-70 Positive | | |
| --- | --- | --- | --- | --- | --- | --- | --- |
| miRNA ID | Normal | Stage 0 | Stage I-II | Stage III-IV | Stage 0 | Stage I-II | Stage III-IV |
| hsa-miR-205 | 11.42 | 13.07 | 14.13 | 12.18 | 7.10 | 6.47 | 8.97 |
| hsa-miR-652 | 12.81 | 13.88 | 12.43 | 13.48 | 7.86 | 11.79 | 10.23 |
| hsa-miR-532-3p | 15.24 | 14.13 | 14.58 | 16.26 | 12.90 | 11.82 | 11.92 |
| hsa-miR-140-5p | 16.67 | 13.97 | 14.70 | 15.72 | 13.81 | 13.36 | 10.17 |
| hsa-miR-150 | 21.41 | 24.90 | 24.90 | 24.90 | 23.29 | 21.31 | 23.29 |
| hsa-miR-10a | 14.55 | 10.17 | 11.44 | 11.21 | 7.74 | 9.81 | 8.59 |

TABLE 1-continued

List of differentially expressed miRNAs between the ZAP-70 positive and ZAP-70 negative samples. The miRNAs with higher levels in ZAP-70 positive plasma are those below the line.

| | | ZAP-70 Negative | | | ZAP-70 Positive | | |
|---|---|---|---|---|---|---|---|
| MiRNA ID | Normal | Stage 0 | Stage I-II | Stage III-IV | Stage 0 | Stage I-II | Stage III-IV |
| hsa-miR-29a | 17.16 | 19.29 | 18.37 | 19.20 | 17.06 | 16.67 | 16.50 |
| hsa-miR-769-5p | 12.15 | 9.77 | 10.20 | 10.51 | 8.54 | 7.28 | 8.94 |
| hsa-let-7b | 17.06 | 15.38 | 16.07 | 15.70 | 14.37 | 13.76 | 13.36 |
| hsa-miR-20b | 17.99 | 15.84 | 15.31 | 16.33 | 15.84 | 13.97 | 12.43 |
| hsa-miR-103 | 13.97 | 11.82 | 11.82 | 13.39 | 9.89 | 12.59 | 9.55 |
| hsa-miR-432 | 6.47 | 17.16 | 17.59 | 17.65 | 17.03 | 15.27 | 15.31 |
| hsa-miR-193a-5p | 18.21 | 15.15 | 16.14 | 15.38 | 14.96 | 12.06 | 15.70 |
| hsa-miR-26b | 17.32 | 12.81 | 12.37 | 14.65 | 12.99 | 10.83 | 12.11 |
| hsa-miR-93 | 19.56 | 17.26 | 17.32 | 18.37 | 17.73 | 15.49 | 15.90 |
| hsa-let-7e | 18.57 | 14.96 | 13.18 | 14.51 | 12.27 | 13.72 | 13.07 |
| hsa-miR-885-5p | 19.20 | 13.92 | 13.61 | 15.09 | 13.88 | 13.44 | 12.06 |
| hsa-miR-744 | 15.70 | 10.60 | 13.22 | 14.01 | 12.66 | 14.51 | 14.13 |
| hsa-miR-378 | 16.81 | 16.98 | 19.56 | 18.31 | 19.38 | 19.96 | 19.13 |
| hsa-miR-335 | 15.77 | 9.04 | 11.36 | 12.00 | 11.72 | 12.90 | 11.63 |
| hsa-miR-301a | 14.29 | 10.08 | 12.27 | 11.92 | 13.03 | 12.51 | 12.71 |
| hsa-miR-491-5p | 10.92 | 17.49 | 15.20 | 14.70 | 17.49 | 15.31 | 18.68 |
| hsa-miR-505* | 12.59 | 7.28 | 7.10 | 9.57 | 9.59 | 8.54 | 10.01 |
| hsa-miR-10b* | 13.22 | 8.31 | 10.33 | 10.26 | 10.23 | 12.93 | 10.29 |
| hsa-miR-636 | 13.84 | 9.70 | 8.87 | 10.92 | 11.59 | 11.16 | 11.89 |
| hsa-miR-486-5p | 16.50 | 18.21 | 19.20 | 19.38 | 20.65 | 20.65 | 20.99 |
| hsa-miR-375 | 19.47 | 12.93 | 16.26 | 15.31 | 16.50 | 17.73 | 15.93 |
| hsa-miR-875-5p | 12.27 | 16.74 | 18.83 | 16.67 | 18.14 | 20.79 | 19.29 |
| hsa-miR-212 | 12.30 | 11.92 | 10.26 | 11.12 | 12.46 | 13.81 | 13.44 |
| hsa-miR-483-5p | 18.10 | 18.04 | 18.04 | 17.06 | 19.47 | 19.65 | 21.41 |
| hsa-miR-206 | 12.18 | 15.17 | 16.50 | 15.84 | 18.31 | 17.32 | 19.38 |
| hsa-miR-494 | 13.03 | 6.36 | 6.56 | 7.97 | 9.14 | 8.81 | 11.33 |
| hsa-miR-363 | 11.52 | 10.96 | 13.68 | 14.24 | 16.02 | 16.53 | 16.71 |
| hsa-miR-144* | 16.26 | 10.36 | 6.72 | 8.42 | 12.15 | 12.43 | 12.66 |
| hsa-miR-19b-1* | 13.07 | 11.24 | 14.18 | 13.03 | 16.81 | 19.38 | 19.56 |

The levels of these plasma miRNAs constitute new and informative biomarkers in CLL diagnosis.

We also identified regulatory networks associated with ZAP-70 expression, which permit therapeutic intervention targeted toward ZAP-70 positive subjects. This circuit consists of miR-181a, miR-23b, nuclear receptor subfamily 6, group A, member 1 (NR6A1) and ZAP-70, as shown in FIG. 9.

The genes and miRNAs involved in the putative regulatory network are indicated. Overexpression of NR6A1 and ZAP-70 occurs when levels of miR-23b and miR-181a are lower. The degree of lower expression is indicated by intensity of shading. The miRNA expression levels in different ZAP-70 expression status are indicated as "+"—ZAP-70 positive and "−"—ZAP-70 negative samples.

Although the levels of miR-23b and miR-181a in plasma showed little change, either between patients with different ZAP-70 expression status or among different disease stages, in CLL cells, the levels of both miR-23b and miR-181a showed significant decreases in both ZAP-70 positive and negative samples. The effect of miR-181a on ZAP-70 is mediated in part through NR6A1, a Predicted target of miR-181a as well as a potential transcription factor regulating the ZAP-70 gene. The NR6A1 receptor is encoded by a gene with 10 exons spanning a 240 kb region in the genome, and the miR-181 family member miRNAs, miR-181b-2 and miR-181a-2, are located within the NR6A1 gene in the second intron (with a transcription orientation opposite to NR6A1). The expression patterns of the "gene pair" usually show negative correlations, probably because of regulatory effects and the possibility of forming unstable double-stranded RNA from the primary transcripts. The interaction between miR-181a and NR6A1 may occur by both miRNA-mRNA interaction and transcription competition.

In particular, lower miR-181a levels imply higher NR6A1 mRNA and protein levels, as well as higher transcription rates of the NR6A1 gene. As the levels of miR-181a are down in both ZAP-70 positive and negative cell samples, this suggests involvement of additional factors on the induction of NR6A1 and ZAP-70 genes. Nevertheless, the evidence for the model shown above provides a therapeutic entry point using, for example, RNAi like technology to modulate (enhance preferably) the levels of miR-181 and/or miR-23b and/or NR6A1 to target ZAP-70 positive CLL.

Thus, the invention has a number of specific aspects as follows.

1. A method to screen subjects for a positive indicator of chronic lymphocytic leukemia (CLL) which method comprises assessing plasma of at least one test subject for total miRNA level and comparing said miRNA level to that of one or more normal subjects, whereby a statistically significant increase in level of total miRNA in said test subject is an indicator that said subject may have CLL.

2. A method to assess aggressiveness of CLL in a subject, which method comprises assessing the plasma of said subject for miR-20a and/or miR-16 whereby a lower level of said miR-20a and/or miR-16 in said subject as compared to normal subjects indicates the CLL of said subjects is aggressive.

3. A method to evaluate a subject for the presence of CLL which method comprises determining the levels of miR-202 and/or miR-708 and/or miR-363 and/or miR-769-5p and/or miR-34a and/or miR-564 and/or miR-34a* and/or miR-27a* and/or miR-584 to determine a spectrum of levels comprising at least three of said miRNA species and comparing said spectrum to the spectrum of said at least three miRNAs in normal subjects whereby a spectrum having the characteristics set forth for said miRNAs in FIGS. 7A and 7B indicates the presence of CLL in said subject.

4. A method to assess a subject for having CLL which method comprises assessing the plasma of said subject for the levels of miR-29a and/or miR-150 and/or miR-195 and/or miR-222, wherein statistically significant elevated assessed levels of said miRNAs as compared to normal subjects indicates the presence of CLL in the subject.

5. A composition that modulates the level of miR-23 and/or miR-181a for use in a method to treat CLL in a subject by effecting a diminution of expression of NR6A1 in said subject.

6. A method to effect apoptosis in malignant cells of a CLL subject which method comprises downregulating the expression of BCL-2 by modulating the level of miR-93 and/or miR-23b and/or miR-181a and/or miR-185 and/or miR-15a and/or miR-221 and/or miR-222 in said subject.

7. A method to monitor the progress of CLL in a subject which method comprises determining the level of miR-30e and/or miR-363 in the plasma of said subject over time, whereby if the level of said miR-30e decreases over time and/or the level of miR-363 increases over time, the CLL is indicated as progressing in said subject.

8. A method to treat CLL by effecting a diminution of expression of NR6A1.

BRIEF DESCRIPTION OF THE DRAWINGS

FIG. 5 shows putative regulatory network associated with BCL2 and ZAP-70 expression.

FIG. 8 shows NR6A1 binding region and matrix were obtained from Biobase BKL TRANSFAC® and ExPlain™ databases. Binding nucleotides were highlighted on the promoter region of the ZAP-70 gene (obtained from the Transcriptional Regulatory Element Database, Cold Spring Harbor, N.Y.) (SEQ ID NO:1).

MODES OF CARRYING OUT THE INVENTION

Figure 1:
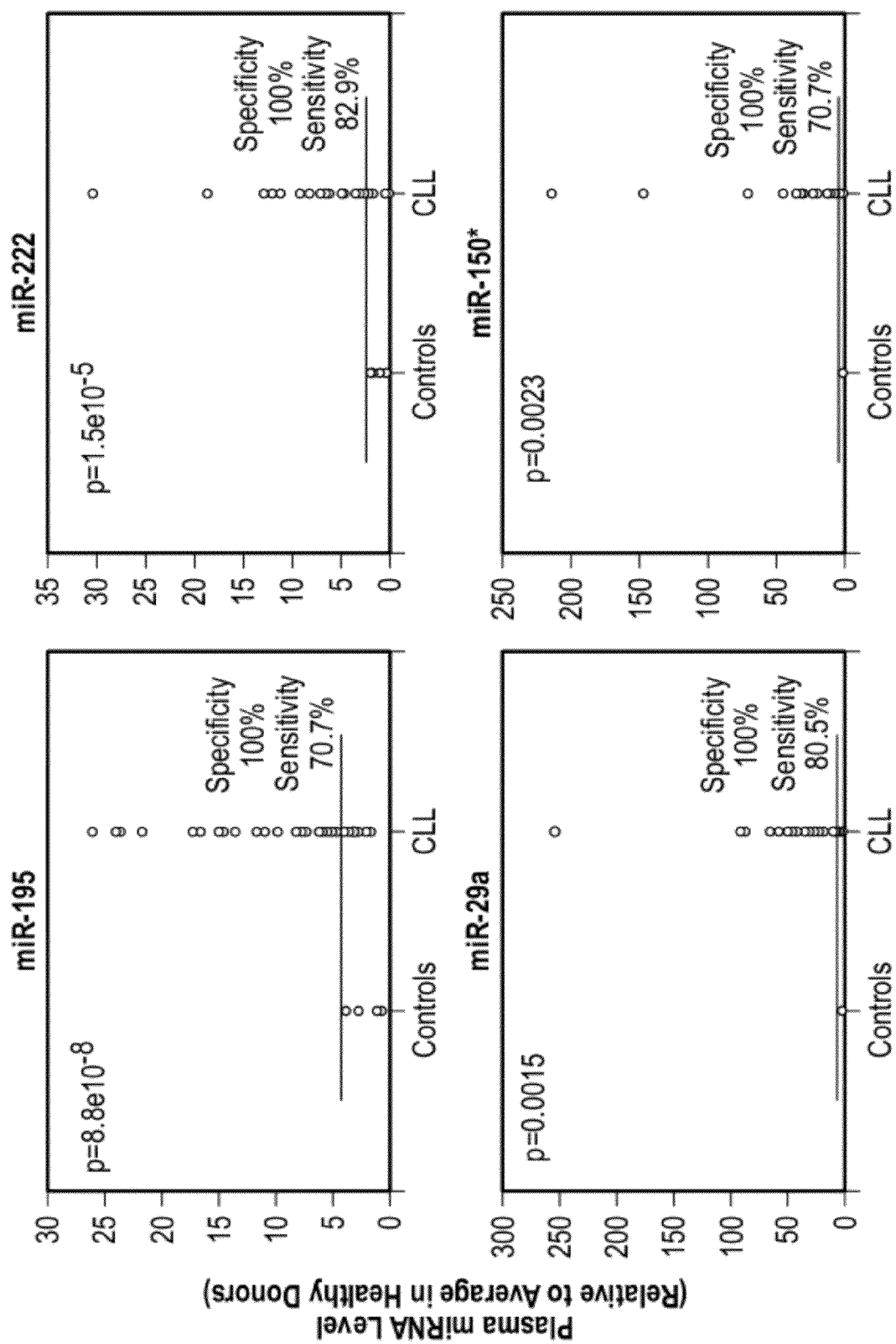
FIG. 1 shows detection of CLL by the levels of specific miRNAs in plasma. Plasma levels of selected miRNAs were determined by RT-qPCR in 41 CLL patients and 8 healthy controls. Ct values were normalized by using synthetic spiked-in C. elegans miRNAs and fold changes were calculated relatively to the average expression in plasma of healthy controls. The line indicates a 100% specificity threshold. P-values were obtained by 2-sided t-test.

In CLL malignant B lymphocytes are nonfunctional and have defects in the cellular apoptotic machinery. Cytogenetic abnormalities are often found in these B cells. Although the nature and number of aberrations may vary, a few consistent aberrations are observed in CLL B cells, including trisomy of chromosome 12 and deletions of 13q14.3, 17p13 and 11q22.

Like many other cancers, the diagnosis of the disease is often delayed due to the lack of symptoms in early stages. The abnormal expressions of certain T cell markers by CLL B cells, namely CD5, CD 184, and ZAP-70, have been helpful in the stratification of the disease [1]. For example, overall survival is significantly better for ZAP-70 negative cases than for ZAP-70 positive. ZAP-70 is primarily a T and NK cell marker in differentiated cells and also plays a role in the transition of pro-B to pre-B cells in the bone marrow. Thus ZAP-70 positive CLL seem to represent less differentiated cell populations and have a more aggressive cancer phenotype with marker characteristics of a cell state "earlier" in the B differentiation pathway. Although CLL remains an incurable disorder, early stage detection and treatment can control disease progression, as late stage patients are often unresponsive to various treatments. Even though CLL often presents with a heterogeneous pathology in the clinic, most patients receive a few standardized treatments based primarily on limited clinical parameters such as Rai or Binet staging which classify CLL patients based on the spreading of these diseases and cytogenetic characterization, underlining the need for more informative diagnostic markers with better clinical significance [2, 3].

Since the recent description of circulating extracellular RNAs in plasma, they have become an attractive source of new nucleic acid-based biomarkers. The observation of stable microRNAs (miRNAs) in plasma has recently been reported to be correlated with numerous human diseases. MicroRNAs belong to the class of small non-coding RNA molecules (~20 nucleotides) and affect biological functions either by post-transcriptional silencing or stimulating transcript degradation. It is estimated that the expression of 20 to 30% of protein-coding genes may be affected by either one or multiple miRNAs. It is believed that the levels of miRNAs are precisely controlled in the cells to assure proper cellular function and differentiation; therefore, aberrant expression of miRNA are commonly observed in pathological processes, including oncogenesis [4]. One commonly observed chromosomal aberration in CLL is the deletion of chromosomal 13q14.3, a region containing miR-15a and miR-16, which suggests the possible involvement of these miRNAs in the pathogenesis of CLL [5]. In addition, an aberrant cellular miRNA expression profile in CLL B cells has been described [6], further supporting a relationship between miRNA expression and disease progression. Cellular miRNA expression spectra also correlated with well-accepted prognostic factors including ZAP-70 expression and IgVH mutation in CLL patients [7]. Recent studies also demonstrated the decrease of miR-29c and miR-223 levels in cells during the progression of the disease and could be used to predict treatment-free survival and overall survival [8].

Prior studies have reported the presence of tumor-derived, low molecular weight RNAs (miRNAs and ncRNAs) in plasma of patients with solid tumors [9]. In the present study, our aim was to explore the changes of extracellular miRNA spectra in CLL samples to provide more accurate assessment of the disease, and improve the molecular classification of CLL. Based on our findings, specific miRNA signatures are associated with different CLL stages and cytogenetic alterations. Plasma miRNAs as shown below constitute new and informative biomarkers in CLL diagnosis, as well as guideposts to therapy.

Thus, as described in the studies conducted in human patients, additional miRNA markers are found useful in the plasma both to indicate the presence of the condition and its stage of progression.

As used herein "a" or "an", etc., indicates one or more than one unless otherwise indicated. In addition, documents cited herein are hereby incorporated by reference for the purpose for which they are cited.

The following example is intended to illustrate but not limit the invention.

Example 1

In this study, we investigated the changes of plasma miRNA spectrum from a cohort of CLL patient plasma samples. The B CLL prognosis markers, ZAP-70 expression level and IgVH mutation status from these samples were also determined. To identify miRNA with potential clinical applications, we first profiled plasma miRNA spectrum with TaqMan® microRNA low density arrays (assessing the levels of 667 individual miRNAs) using nine pooled samples including healthy controls, 6 pooled CLL patients based on disease stages and ZAP-70 expression status, patients with multiple myeloma (MM), and patients with hairy cell leukemia (HCL). The miRNAs with altered expression levels were then verified with individual samples.

Material and Methods

Patients. Healthy controls and patients affected by hematologic malignancies were recruited from a single institution (Centre Hospitalier de Luxembourg) after obtaining a written informed consent in accordance with the Declaration of Helsinki. The study obtained the approval of the 'Comité National d'Ethique de la Recherche' of Luxembourg. A cohort of 41 CLL patients was enrolled into this study including different Rai stages (0 to IV) and treatment histories. Clinical details of the CLL patients are presented in Table 4. Sex- and age-matched patients with multiple myeloma (MM; N=7) and hairy cell leukemia (HCL; N=4) were also recruited together with local healthy controls (N=8).

Plasma Preparation.

All plasma samples were prepared by sequential centrifugations from whole blood collected in EDTA. First, blood tubes were centrifuged 10 min at 1,000×g to separate cells from fluids. Plasma was then centrifuged 20 min at 10,000×g to eliminate platelets and debris, and then filtered through 0.22 µm membrane (MILLEX® GP, Millipore, Belgium) to remove micrometer-sized vesicles and other contaminating membranes before RNA extraction.

After removal of plasma, an equivalent volume of PBS was added to reconstitute the pellet and the solution was layered onto Lympho isolation medium (MP Biomedicals, France) to isolate lymphocytes. For CLL patient samples, the cells collected contained >95% B cells. Contaminating erythrocytes were eliminated by incubation 5 minutes in RBC lysis buffer. For MM, HCL, and samples from healthy controls, a B-cell-enrichment process was performed by negative selection with Dynabeads® CD2 and CD14 (Dynal Biotech, Norway).

MicroRNAs Expression Profiling on RNA Pools.

For miRNA profiling, total RNA was extracted from 300 µl of plasma with the miRNeasy® kit (Qiagen, Germantown, Md.) as described [10]. The quality and quantity of RNA were assessed by using an Agilent 2100 Bioanalyzer (Santa Clara, Calif.).

The RNA samples were pooled according to their disease stage by mixing equal amounts of RNA from each individual in the group. Twelve microliters of RNA from each pooled sample were dried and resuspended in 3 µl of water. The cDNA was then generated using Megaplex™ (Invitrogen) RT Primer pools. Pre-amplification was performed using 2.5 µl cDNA according to the manufacturer's protocol (Applied Biosystems, Foster City, Calif.). The resulting samples were diluted to 100 µl, and 9 µl of each were loaded onto TaqMan® Array Human miRNA Panels A and B (Applied Biosystems). PCR results were analyzed with SDS 2.3 (Applied Biosystems). Global mean was used to normalize the expression levels among different samples.

MicroRNA candidates were then investigated by qPCR on individual plasma samples (CLL, N=41) in a blinded manner. The RT and PCR were performed with miRNA-specific primers in small-scale reactions according to a previous report [9]. For plasma RNA, rather than a fixed RNA mass, a fixed volume of 1.67 µl of RNA eluate was reverse transcribed using the TaqMan® miRNA Reverse Transcription Kit and miRNA-specific stem-loop primers (Applied Biosystems). The RT products (5 µl) were diluted with 28.9 µl of water and 2.25 µl were combined with 2.5 µl of TaqMan® 2× Universal PCR Master Mix, No AmpErase UNG and 0.25 µl of TaqMan® miRNA Assay (Applied Biosystems) for amplification in a total volume of 5 µl. The fluorescence intensity was monitored with the 7300 Real-Time PCR System® (Applied Biosystems). For each plasma miRNA, the relative expression level was calculated using *C. elegans* miRNAs as exogenous controls and the mean of Ct values from healthy controls as a calibrator. When the Ct value was greater than 35, the expression of the miRNA was considered to be negative in the sample analyzed.

For analysis of cellular miRNAs, total RNAs were extracted with the miRNeasy® kit (QIAGEN, The Netherlands). Reactions were performed as for plasma miRNAs. Twenty nanograms of cellular total RNA were reverse transcribed. For mRNAs, nuclear receptor subfamily 6, group A, member 1 (NR6A1), flotillin-2 (FLOT2) and peptidylprolyl isomerase A (cyclophilin A, PPIA) were amplified by RT-qPCR with specific TaqMan® probes and primers (Applied Biosystems). FLOT2 and PPIA were used as house-keeping genes. One microgram RNA was reverse transcribed with the RT core kit (Eurogentec) and cDNA was amplified with the TaqMan® Universal Master Mix II, no UNG (Applied Biosystems).

Analysis of ZAP-70, CD38, and Sequence Analysis of IgVH.

Analysis of CD38 on the surface of CLL B cells was performed by flow cytometry following standard protocols and recommendations. Threshold for CD38 positivity was set at 7%. The ZAP-70 status was verified by RT-PCR as described by others [1]. The analysis of expressed IgVH gene was done by PCR followed by sequencing (98% homology as a threshold) as reported before [36].

Statistical Analysis.

The statistical analysis of miRNAs expression levels was performed by t-test (2-sided). Only when p-values were less than 0.05, differences in expression were considered to be statistically significant. To evaluate the strength of the association between miRNAs expression in plasma and/or in cells, the Pearson product-moment correlation coefficient (denoted by r) and accompanying p-value were calculated. Acuity® 4.0 (Molecular Devices Corporation, CA) was used for unsupervised two-dimensional hierarchical clustering of miRNAs expression in plasma of CLL patients obtained by RT-qPCR.

Results

Our results showed increased levels of total miRNA in the plasma of B cell related malignancies.

Figure 6:
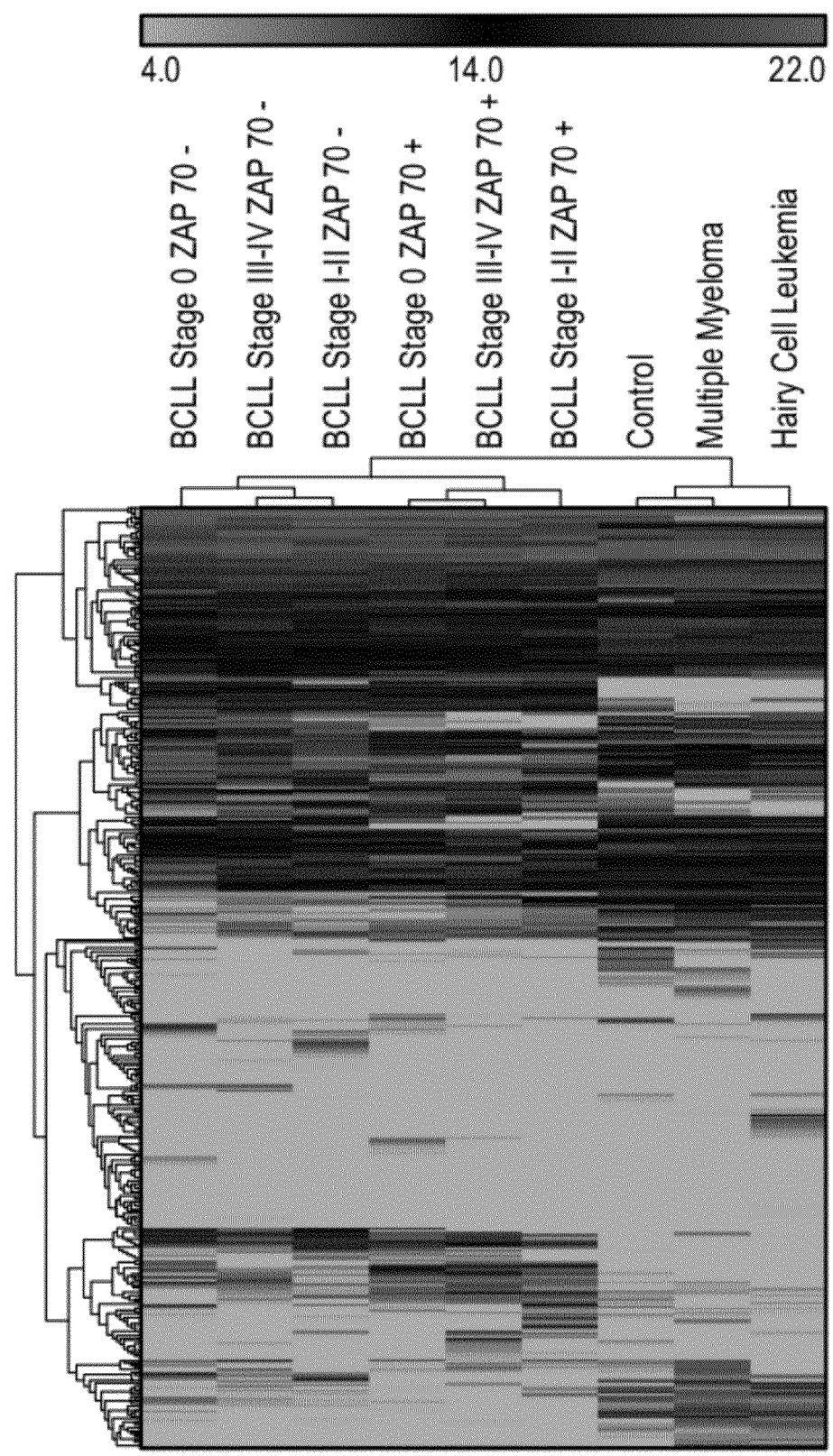
FIG. 6 shows unsupervised hierarchical clustering based on the global plasma miRNA spectra on pooled samples. The miRNA profile can be grouped into three major groups, the ZAP-70 positive samples, the ZAP-70 negative samples and a group containing normal, MM and HCL samples

Based on the results of global plasma miRNA profile, the samples were clustered into three major groups, the ZAP-70 positive samples, the ZAP-70 negative samples and a group containing normal, MM and HCL samples (FIG. 6). Similar to prior findings for solid tumors, a higher number of detectable circulating miRNAs was found in CLL plasma samples (average n=296) compared to normal control plasma (n=230), a 28% increase. A similar trend was also observed in other hematologic malignancy samples tested, MM plasma sample had 256 detectable miRNAs, an 11% increase, and HCL has 260 detectable miRNA species, a 13% increase compared to normal. The plasma samples from ZAP-70 positive CLL patients had much higher detectable miRNAs than the ZAP-70 negative samples, 333 detectable miRNA species in ZAP-70 positive vs. 256 detectable miRNA species in ZAP-70 negative at samples Stage 0, approximately 310 vs. 225 at Stage II and 325 vs. 240 at stage III-IV.

Examining the list of the 20 most abundant miRNAs in all our plasma samples, a significant number of miRNA species including miR-150, miR-19b, and miR-92a, miR-223, miR-320, miR-484 and miR-17 were highly abundant in all the samples (Table 1). A few of these highly abundant miRNAs show some interesting changes, for example the miR-20a and miR-16 were highly abundant in all the samples except for ZAP-70 positive. miR-223 was the most abundant miRNA species in normal human plasma; however, in ZAP-70 negative CLL samples the miR-150 was the most abundant. In ZAP-70 positive samples either miR-92 or miR-484 was the most prominent.

Figure 7A:
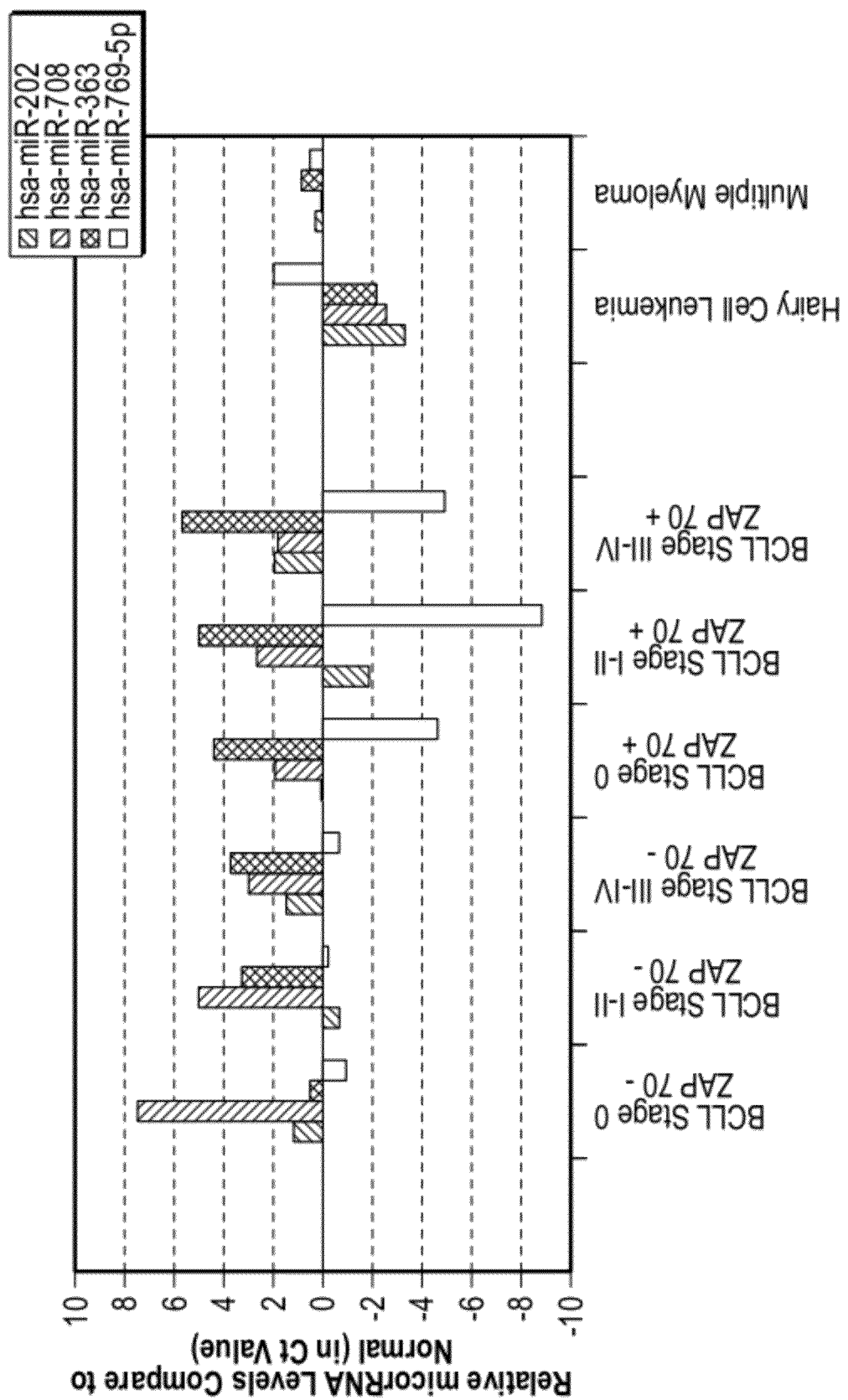
FIGS. 7A and 7B show several microRNA species showed distinct profiles between CLL and HCL (A), and CLL and MM (B).
Figure 7B:
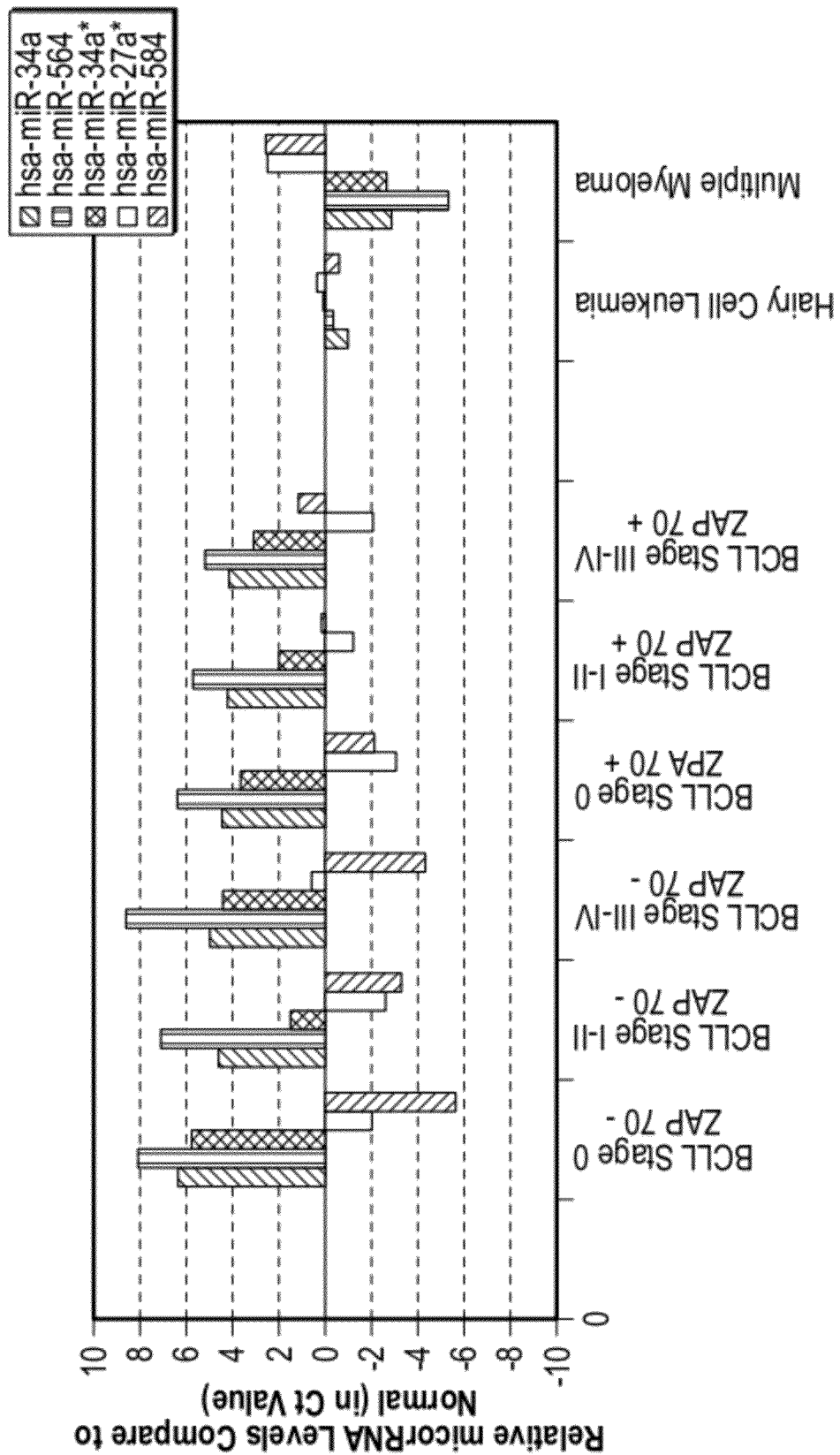
Figure 9:
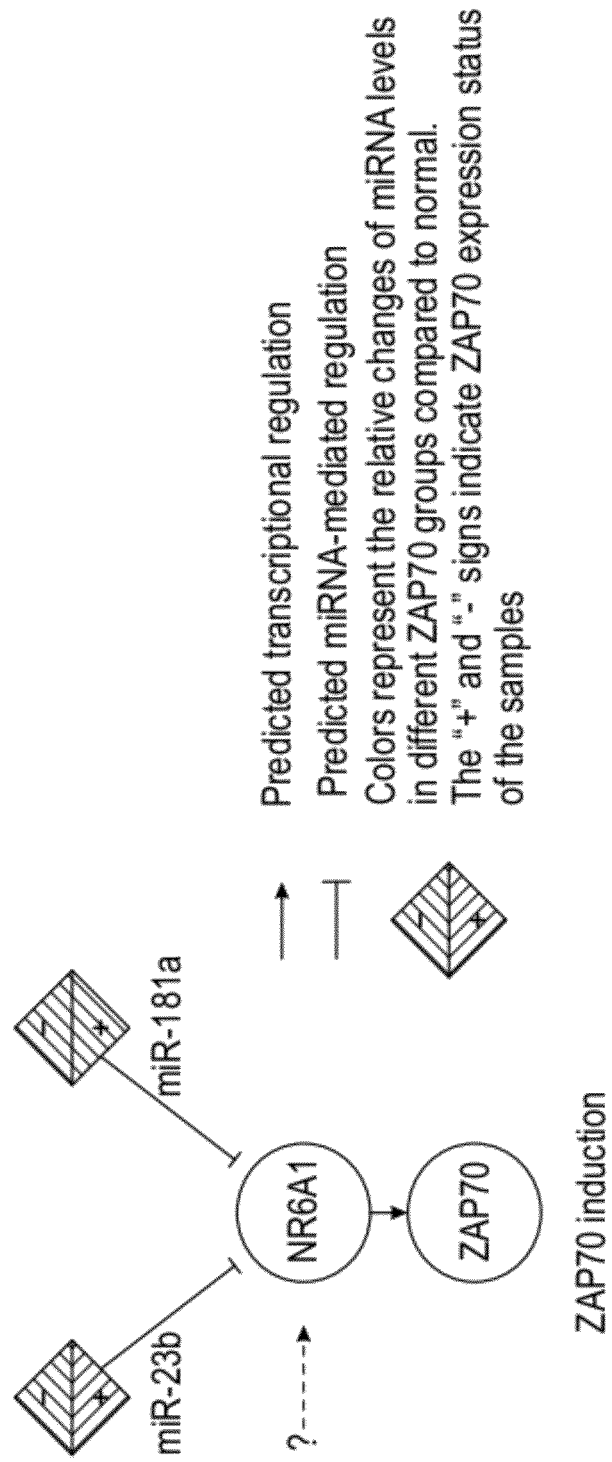
FIG. 9 shows a regulatory network associated with ZAP-70 expression which permits therapeutic intervention targeted toward ZAP-70 positive subjects. This circuit consists of miR-181a, miR-23b, nuclear receptor subfamily 6, group A, member 1 (NR6A1) and ZAP-70.

From the pooled global miRNA profiling results, several microRNA species showed distinct profiles between CLL and HCL or MM samples (FIGS. 7A and 7B) which we then followed up with measurements on individual patient samples. We found that the levels of miR-363 and miR-708 were lower in HCL but higher in all CLL samples with no significant difference in MM (FIG. 7A), while miR-34a and miR-564 were lower in MM but higher in all the CLL samples with no significant changes in HCL compared to normal (FIG. 7B). Among the CLL samples, there were a number of miRNA species showing differences based on the ZAP-70 expression status (Table 3). For instance, the levels of miR-205, miR-29a and miR-652 are higher in ZAP-70 negative samples compared to ZAP-70 positive samples, while miR-19b and miR-144* were higher in ZAP-70 positive samples. In addition, a number of miRNAs also showed progressive changes along with the severity of the disease, for example miR-30e concentration in plasma continues to decrease while miR-363 level continues to increase as disease progresses regardless of their ZAP-70 expression status. These miRNAs classify CLL patients by stage, and monitor progression.

We also found that levels of specific circulating miRNAs can be used to identify different hematological malignancies.

To assess the potential of selected miRNAs as CLL markers, 27 miRNAs showing changes on its levels among different pooled CLL plasma samples were chosen for further study on individual samples including 8 normal plasma samples, 41 CLL, 7 MM and 4 HCL samples according to global miRNA profiling results. Among the selected miRNAs, thirteen could discriminate CLL samples from the three other groups of controls (normal, MM and HCL) with high confidence (p<0.05, Table 2). The distribution of plasma levels of four miRNAs (miR-29a, miR-150*, miR-195, and miR-222) for CLL and normal is shown in FIG. 1.

Figure 2:
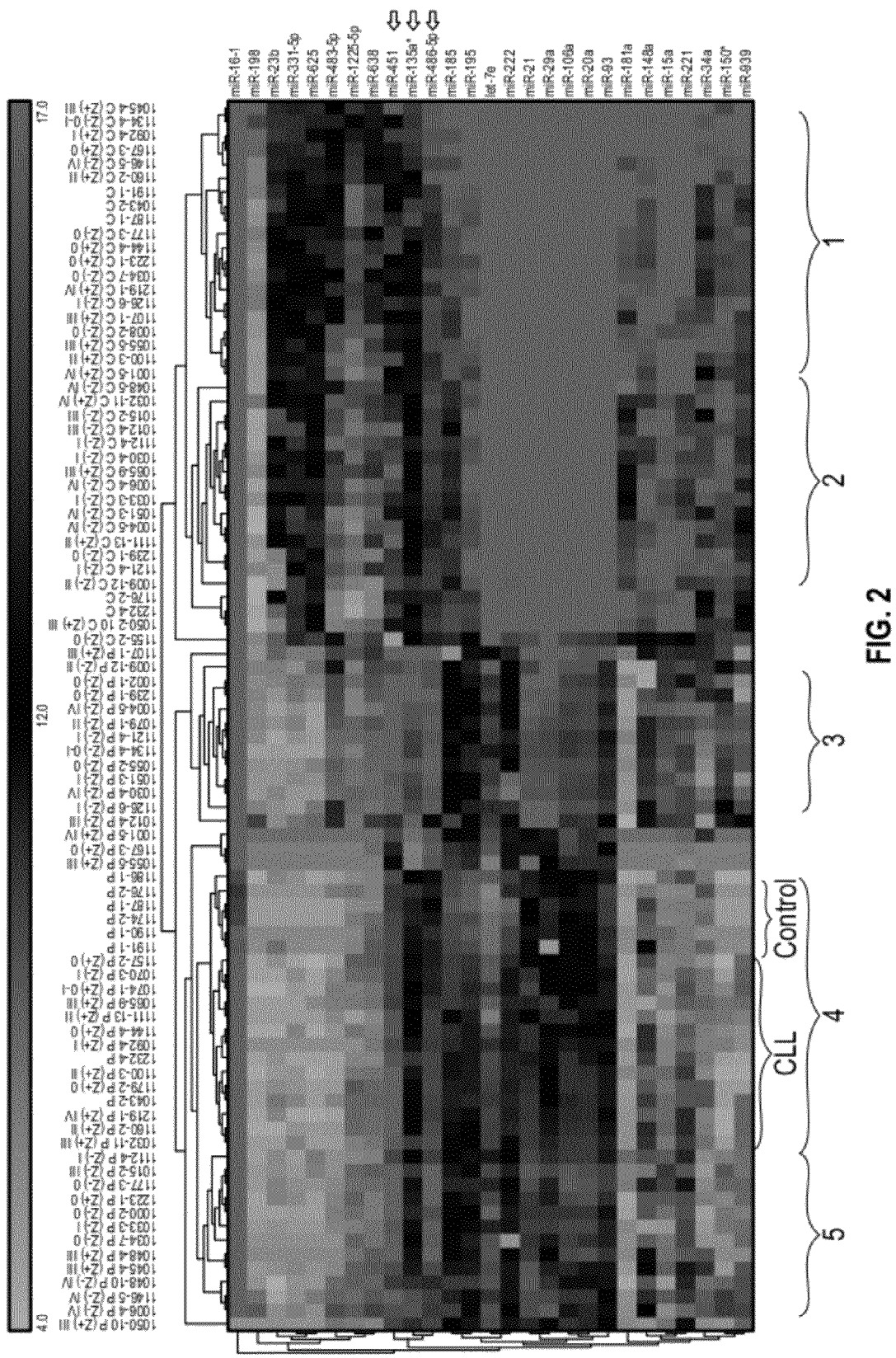
FIG. 2 shows unsupervised hierarchical clustering based on plasma and cellular miRNAs expression. Plasma and corresponding cellular RNAs were analyzed for the expression of selected miRNAs by RT-qPCR. Unsupervised hierarchical clustering was performed using expression fold changes (Ct values) from 27 miRNAs. Medium shade blocks represent miRNAs present at higher level than average while palest blocks represent miRNAs present at a lower level.

The levels of these selected 27 miRNAs were also determined in the corresponding CLL B cells. Using unsupervised hierarchical clustering, the expression profile of the 27 selected miRNAs clearly separated the samples into two main groups, the cell and plasma samples (FIG. 2). The cells, in general, had higher levels of miRNAs than the levels of corresponding species in the plasma, except for miR-135*, miR-451, and miR-486-5P (indicated on FIG. 2). The cellular miRNA spectra further grouped the samples into two main sub-groups (group 1 and 2, FIG. 2); however, there was no clear segregation of samples by either the stage of CLL or the ZAP-70 expression status. Even though there was a general trend, group 1 contains more normal, stage 0, and ZAP-70 positive samples, group 2 contains more stage III and IV samples. The plasma samples were separated by this clustering into three main sub-groups, group 3, 4 and 5. Group 4 contains all the controls and most of the ZAP-70 positive samples (11 out of 18) while the other two groups are mixed with different stages of the CLL samples. Even though the controls and ZAP-70 positive samples were clustered together in group 4 there was a clear separation between them (FIG. 2).

Our results show that ZAP-70 expression status affects the miRNA spectra in both B cells and plasma.

Among the 27 miRNAs selected, a significant fraction of them were found to be over-represented in plasma of the CLL patients compared to healthy controls while most of these miRNAs showed no significant changes in corresponding B cells (Table 3). Even though the changes for some of the miRNAs such as miR-150*, miR-638 in plasma and miR-181a in cells correlates well with disease progression in ZAP-70 negative samples, the majority of the changes among the 27 selected miRNAs do not show significant correlation with disease progression. Several miRNAs, such as miR-185, miR-221, miR-222, miR-451 and miR-93, showed reciprocal changes between plasma samples and corresponding cells, especially in the ZAP-70 negative samples. This reciprocal relationship in the changes of miRNA between intracellular (tissue or cell) and extracellular (plasma) levels is similar to our previous finding in a drug induced liver injury model [10].

Figure 3:
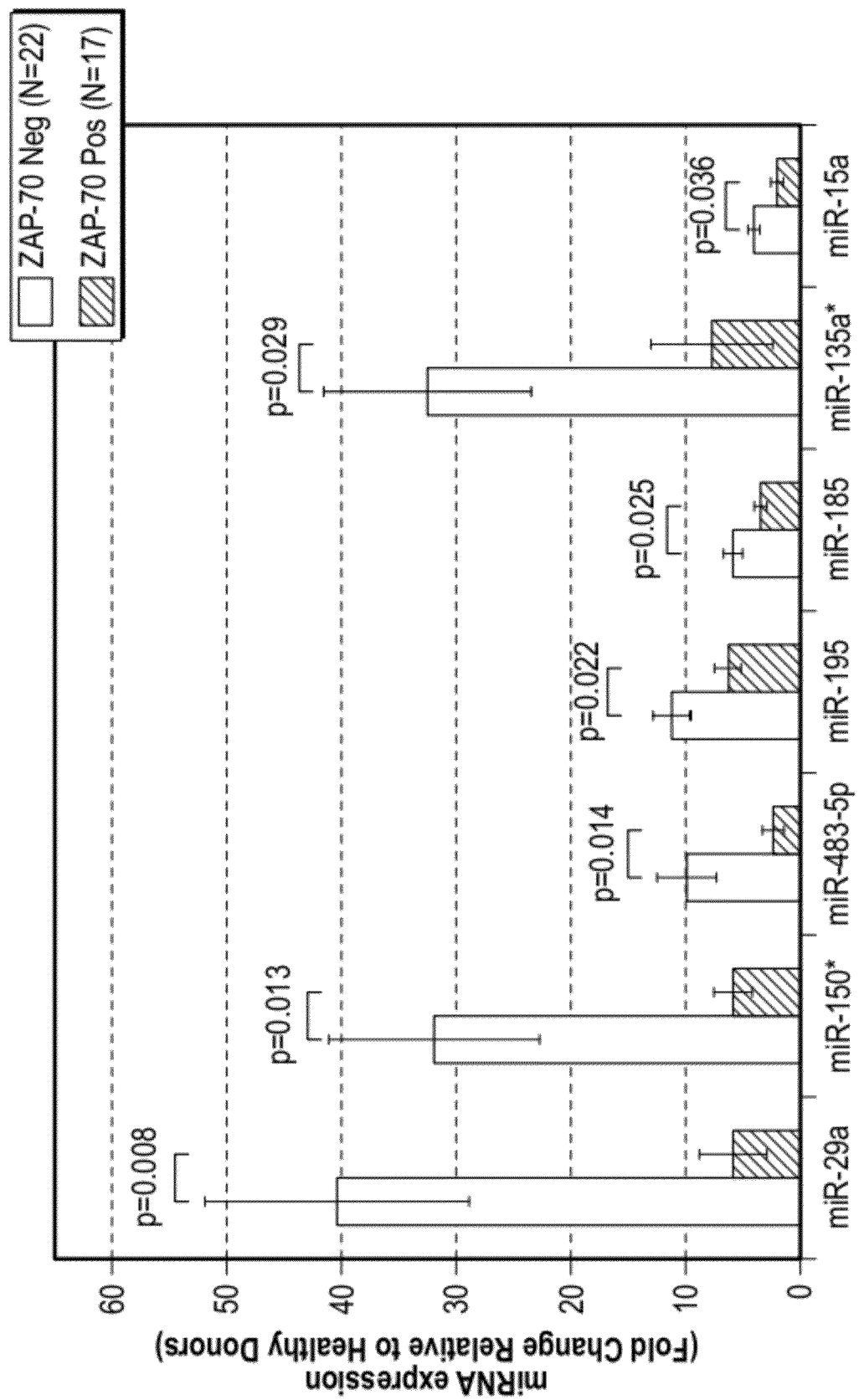
FIG. 3 shows levels of miRNAs in plasma of CLL patients according to cellular ZAP-70 expression. Thirty-nine CLL plasma samples were analyzed for the expression of selected miRNAs by RT-qPCR. The ZAP-70 status of B cells was established by RT-PCR. Data represent the expression fold changes (mean value±standard error) relative to healthy controls for both ZAP-70 positive and negative groups. Exact p-values from 2-sided t-test are presented.

In general, the ZAP-70 negative samples, either the cell or plasma, showed greater variations in the miRNA levels than the corresponding ZAP-70 positive samples. The difference between the two ZAP-70 groups can be as high as 11 fold, such as exhibited by miR-29a levels in CLL plasma samples (Table 3 and FIG. 3). For certain miRNAs, the change of levels can only be observed in ZAP-70 negative samples, such as miR-135a* and miR-150 in plasma and miR-15a and miR-185 in cells (Table 3).

Among the 27 miRNAs selected and studied in CLL cells, 18 of them showed various degrees of change between CLL cells and normal B cells. These 18 differentially expressed miRNAs are predominately between the ZAP-70 negative and normal cells. Comparing the cellular miRNA levels between the two ZAP-70 stages, 14 out of the 27 tested showed some differences when compare to normal; however, only four microRNAs, miR-181a, miR-185, miR-221 and miR-93, are consistently different among all disease stages (Table 3). In contrast to what been observed in certain solid tumors, we did not observe statistically significant correlations between miRNAs levels in cells and corresponding plasma samples. For example, the let-7e, miR-106a, and miR-16-1 levels were increased in plasma but showed no changes in corresponding B cells while the miR-1225, miR-34a, and miR-638 showed significant increases in B cells but almost no observable changes in the plasma (Table 3).

Figure 4:
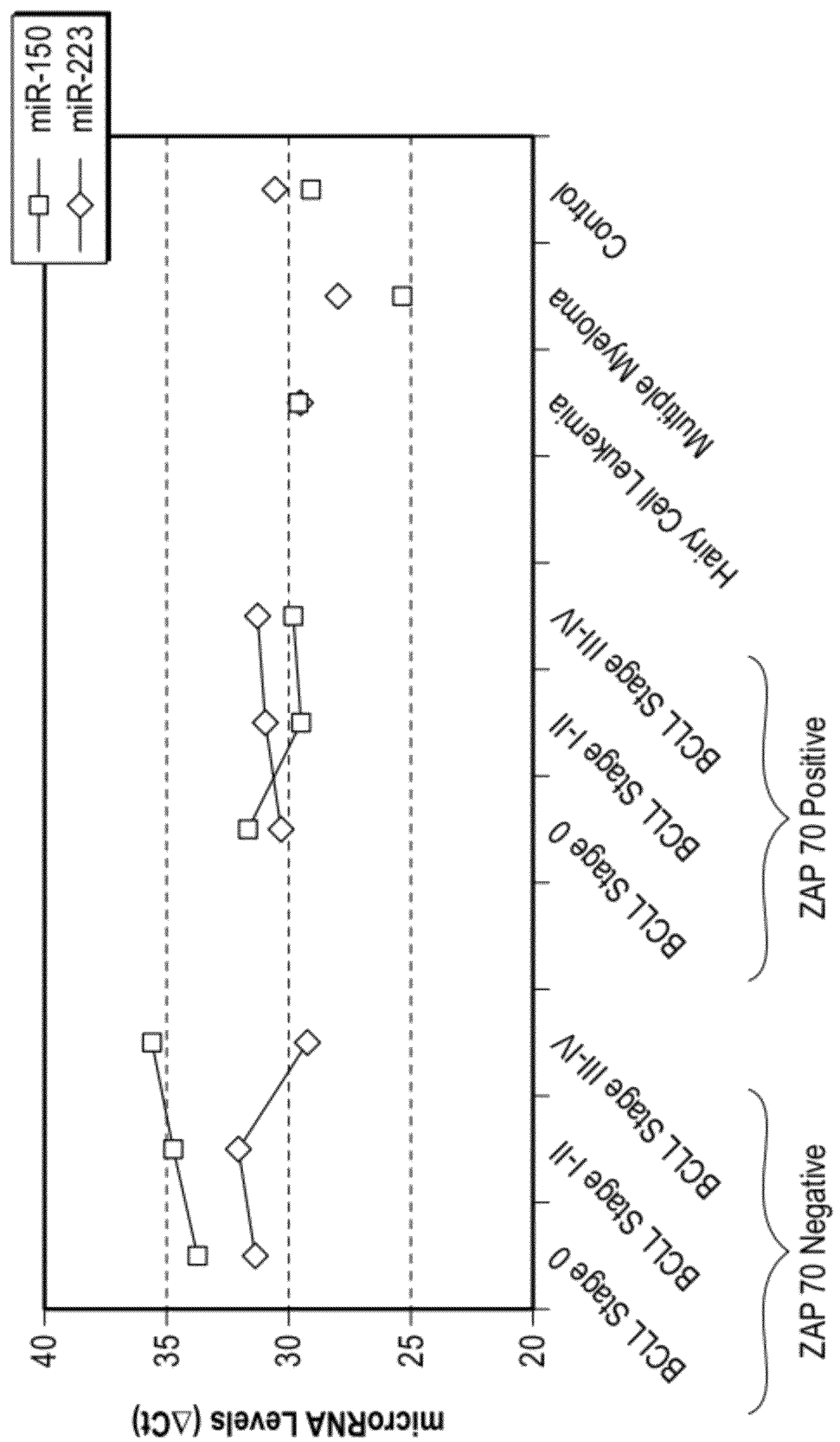
FIG. 4 shows the levels of miR-150 and miR-223 in CLL plasma samples. The levels of miR-150 (black) and miR-223 (gray) on the figure were averaged from individual samples. The levels of miRNAs (in ΔCt values) are showed on Y-axis and the samples are indicated on the X-axis.

We also validated the changes of the most abundant miRNA species between ZAP-70 positive and negative pooled samples, miR-223 in ZAP-70 positive and miR-150 in ZAP-70 negative, on individual plasma samples (FIG. 4). While the level of miR-233 was similar among all the samples, there was a significant increase in the levels of miR-150 in ZAP-70 negative plasma samples. In addition, the level of miR-150 increased along with the severity of the diseases in ZAP-70 negative samples (FIG. 4).

Since there is a strong association between the IgVH mutation status and ZAP-70 expression level, low ZAP-70 expression level usually associated with mutated IgVH [16], we examined the IgVH mutation status from 24 CLL patients by sequencing. Unlike for the ZAP-70 expression status, we did not find significant correlation between IgVH mutation status and plasma miRNAs levels. The levels of specific miRNAs in plasma were also compared to the absolute lymphocyte count (ALC) in the blood. Among the 20 miRNAs showing a significant correlation with ALC (p-value<0.05), miR-29a, miR-150, miR-150*, and miR-483-5p levels in plasma showed strong correlations with ALC (r>0.500 and p-value<0.01) based on Pearson correlation coefficients (Table 5). Conversely, most of other miRNA candidates showed poor correlation with ALC (r<0.300).

Discussion

The presence of an altered miRNA profile in plasma has been reported for different types of solid tumors. These differentially expressed circulating extracellular miRNAs offer the potential for higher sensitivity and specificity in tumor detection compared to existing markers. We investigated the spectra of miRNAs in plasma of CLL patients to see if specific circulating miRNAs could also be used to detect and classify CLL. We observed higher levels of more miRNAs in ZAP-70 positive CLL samples compared to ZAP-70 negative samples and other hematological malignancies, MM and HCL which is consistent with a more diverse cell population in ZAP-70 positive patients.

The change of the most abundant plasma miRNA species in ZAP-70 negative samples from miR-223 to miR-150 may be the result of the changing composition of lymphoid cells in circulation. miR-150 is highly expressed in B cells, the quantitative increase of miR-150 levels in the ZAP-70 negative CLL plasma also correlates well with the stage of the disease. Consistent with our findings in CLL plasma, miR-150 was previously reported to increase in ZAP-70 negative CLL cells [12].

Recent reports have suggested that miRNA are epigenetically down-regulated in cancers [13]. In contrast, higher numbers of detectable miRNA were present in plasma of all hematological malignancies tested in our study including MM, HCL. This may suggest that only a fraction of the circulating miRNAs in patient plasma are from CLL B cells, as previously described [10]. Bone marrow stromal cells are key cells influencing and protecting CLL B cells, which suggests they may play a role in producing circulating miRNAs in B CLL patients.

Many potential gene targets of miRNAs with altered expression patterns in either CLL cell or plasma (Table 3) encode proteins that are over-expressed in CLL cells such as Bcl-2, Mcl-1, p27, Tcl-1 [14-17]. Some of these proteins such as $p27^{Kip1}$ could be jointly regulated by two of the miRNAs over-expressed in CLL plasma (miR-221, and miR-222) and one under-expressed miRNA in cells (miR-181a) [18, 19]. The levels of these miRNAs in plasma show no correlation with blood absolute lymphocyte count in our data. Similarly, the up-regulation of the $p27^{Kip1}$ in cells was reported to be independent of the ALC in CLL [17]. A direct biological relationship between these miRNAs in the plasma and the cellular $p27^{Kip1}$ expression is under investigation. In addition miR-483-5p, elevated 5-fold in plasma of CLL patients, is predicted to target ERK1/MAPK3 which mediates IL-15-induced CLL proliferation [30] and signals CCL-21-driven CLL migration and nodal infiltration [21]. Though most of the miRNA-mRNA interactions are yet to be fully validated, the roles of these plasma miRNAs in CLL present intriguing questions.

Several microRNAs may affect a key network determining the pathology and prognosis of CLL cells, since the spectrum of gene expression in the cell is regulated by elements including both transcriptional factors and miRNAs. Any alterations on the levels of these key elements may lead to profound changes in the gene expression profile in the cell. Two interesting pathological characteristics associated with the CLL B cells are the anti-apoptotic properties associated with up-regulation of the BCL2 gene and the expression of ZAP-70 in more aggressive forms of CLL. To explore the involvement of miRNAs in these two important features of CLL pathology, we collected miRNA interacting gene target information from TargetScan Human V5.1 (located on the World Wide Web at targetscan.org), transcription factor binding site information from MSigDB (located on the World Wide Web at broadinstitute.org/gsea/msigdb/index.jsp) and UCSC genome database (located on the World Wide Web at hgdownload.cse.ucsc.edu/goldenPath/hg18/database) to build a hypothetical miRNA-transcription factor mediated regulatory network that may affect BCL2 and ZAP-70 expression.

Figure 5A:
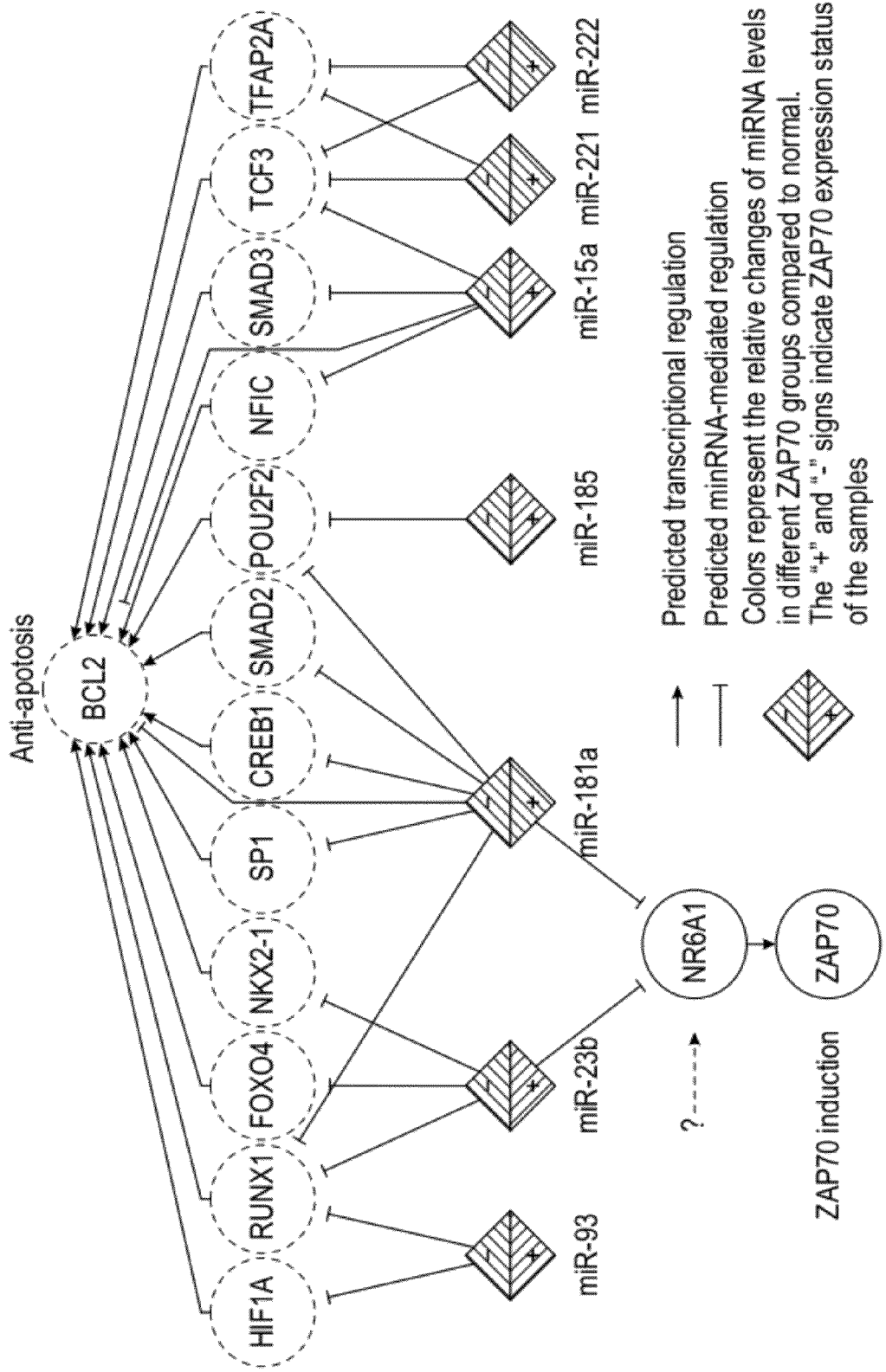
FIG. 5A shows the genes and miRNAs involved in the putative regulatory network are indicated. The dash lines indicate the miRNA-mRNA interaction and solid lines indicate the transcription factor-promoter interaction. The red color indicates over expression of genes or miRNAs compare to normal, while green color indicates lower expression. The miRNA expression levels in different ZAP-70 expression status are indicated as "+" for ZAP-70 positive and "−" for ZAP-70 negative samples. The BCL2 was drawn as a dotted line since the gene expression level was extracted from literature.

The small resulting network contains 7 miRNAs and 13 transcription factors involved in regulating the expression of BCL2 and ZAP-70 genes (FIG. 5a). The seven miRNAs in the network all showed reduced levels in CLL B cells (~1.5 fold decrease), especially the ZAP-70 negative samples, compared to normal controls. Among the seven miRNAs, the miR-181a and miR-15a are predicted to interact with BCL2 directly or indirectly through transcription factors that may recognize the promoter region of BCL2 gene. The miR-23b and miR-181a may also be involved with both BCL2 and ZAP-70 associated transcription factors (through the nuclear receptor NR6A1, see FIG. 8). Note that these circuits driving the expression of BCL2 and ZAP-70 represent coherent effects, which should exhibit switch-like behavior.

Figure 5B:
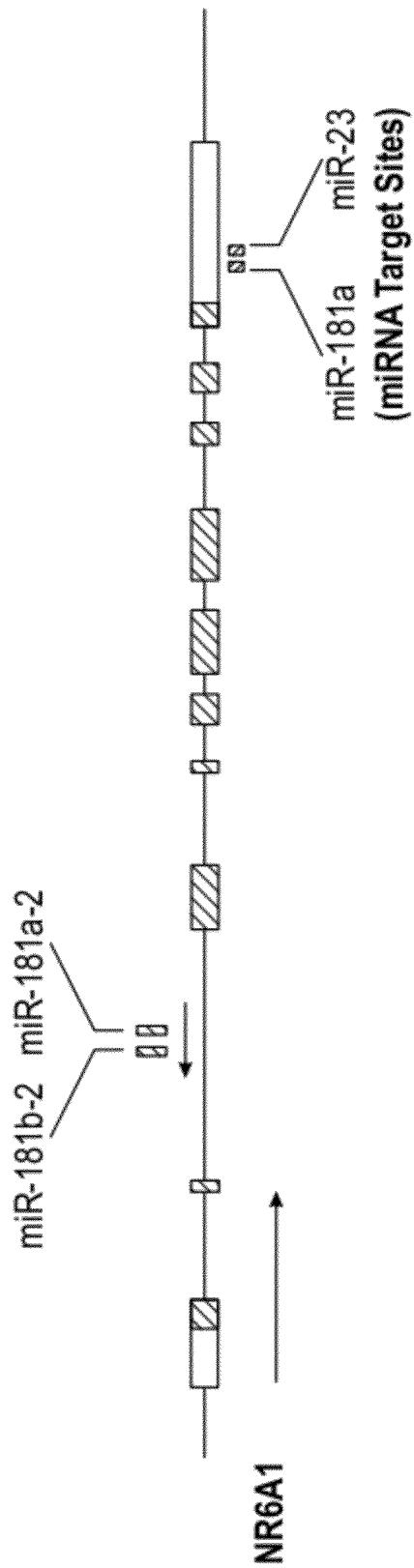
FIG. 5B shows the genomic organizations of the miR-181s and NR6A1. The exons are indicated as black boxes and the 3' and 5' untranslated regions are labeled as open boxes. The transcription orientation is indicated by arrows. The putative miRNA target sites are labeled as short gray lines on the bottom.
Figure 5C:
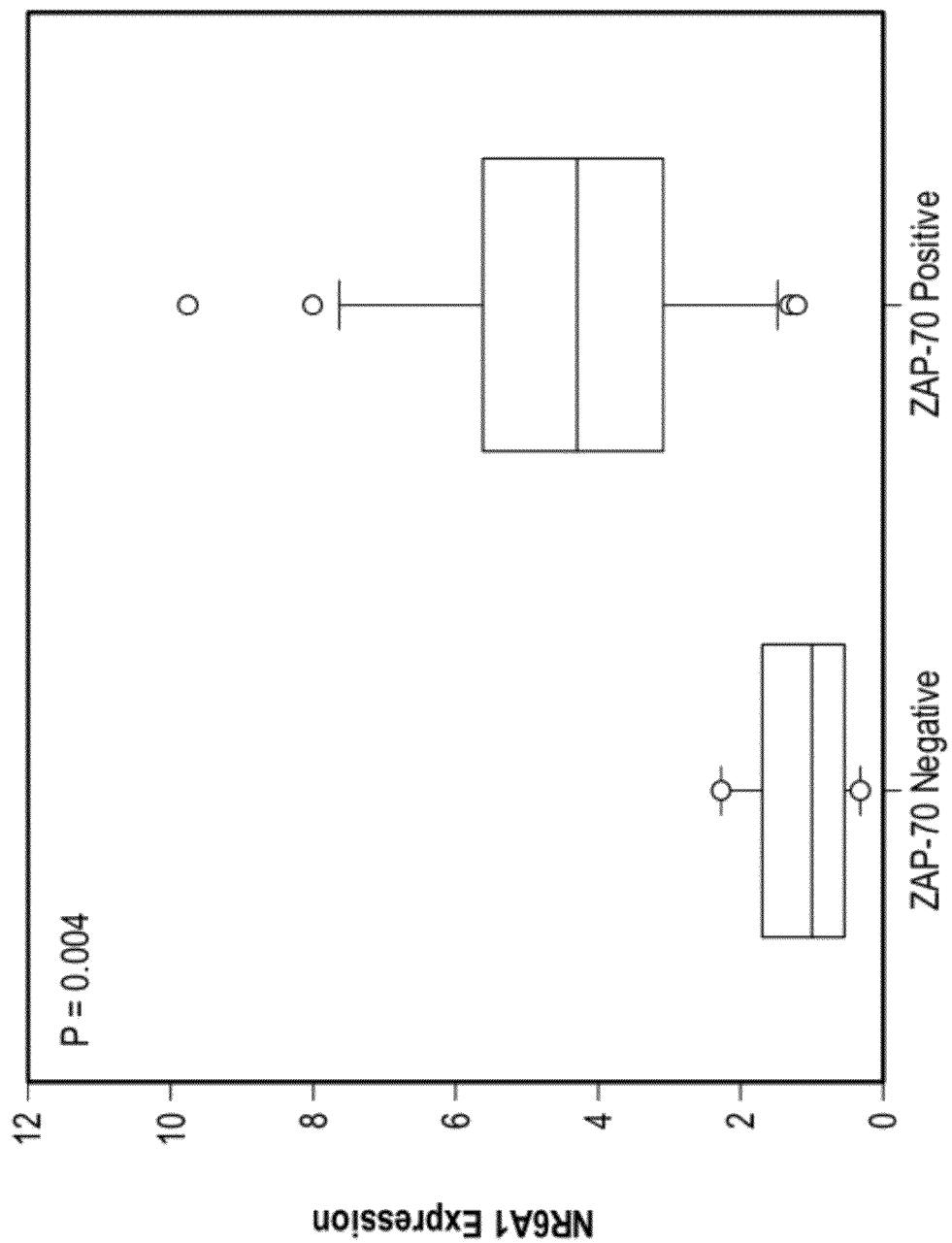
FIG. 5C shows box plot diagrams showing the NR6A1 expression determined by RT-qPCR in CLL samples according to ZAP-70 status. The top of the box indicates the 75th percentile and the bottom the 25th percentile. The line in the middle represents the median. The upper whisker shows the 90th percentile and the lower the 10th percentile. Circles represent the outliers (ZAP-70 negative samples, N=18; ZAP-70 positive samples, N=15). Exact p-value from 2-sided t-test is shown.

The NR6A1 receptor is encoded by 10 exons spanning over 240 kb region in the genome. Some of the miR-181 family member miRNAs, miR-181b-2 and miR-181a-2, are located within the NR6A1 gene in the second intron with a transcription orientation opposite with respect to NR6A1 (FIG. 5b). The level of miR-181a in plasma showed little change, either between the ZAP-70 expression statuses or among different disease stages. However, in the CLL cells, the expression of miR-181a showed significant correlation among different disease stages in both ZAP-70 positive and negative samples (Table 3). Functional transcripts using the opposite strands of the same genomic sequence are an uncommon occurrence, but have been seen: for example, EIF2A and SERP1 on chromosome 3, CDSN and PSORS1C1 on chromosome 3, and TIMP3 and SYN3 on chromosome 22. The expression patterns of these "gene pairs" usually show negative correlations, probably because of regulatory effects and the possibility of forming unstable double-stranded RNA from the primary transcripts. It is possible that the interaction between miR-181a and NR6A1 may occur by both miRNA-mRNA interaction and transcription competition. Lower miR-181a level should then imply higher NR6A1 mRNA and protein levels, as well as higher transcription rate of the NR6A1 gene. A PCR measurement between ZAP-70 positive and negative samples confirmed the higher levels of NR6A1 transcription factor transcript in ZAP-70 positive samples (FIG. 5c), confirming this hypothesis. However, the levels of miR-181a went down in both ZAP-70 positive and negative samples (Table 3) which suggests the possible involvement of additional factors on the induction of NR6A1 and ZAP-70 genes. Thus, the evidence is consistent with the model shown in FIG. 5A.

The development and validation of miRNA biomarkers will be significantly important in improving early cancer detection in order to enhance treatment success rates and to increase the life expectancy of patients with aggressive forms of CLL. We demonstrated from a cohort of CLL patients the feasibility of using circulating miRNA for both detection and stratification of CLL. Levels for several miRNAs are strongly linked to cellular ZAP-70 expression status, but in some cases with little correlation to the staging of CLL (Table 3). The lack of correlation between circulating miRNA profiles and cancer stages was also observed in other cancers.

TABLE 2

Expression levels of differentially expressed miRNAs in BCLL patients: discriminating B-CLL from healthy controls and other hematologic with malignancies

| | B-CLL (N = 41) | Controls (N = 8) | | MM (N = 7) | | HCL (N = 4) | |
|---|---|---|---|---|---|---|---|
| miRNA | Mean ± SEM | Mean ± SEM | p-value† | Mean ± SEM | p-value | Mean ± SEM | p-value |
| miR-150* | 29.07 ± 7.20 | 1.00 ± 0.03 | 0.0023 | 1.43 ± 0.26 | 0.0027 | 0 | NA |
| miR-29a | 24.27 ± 6.79 | 1.07 ± 0.15 | 0.0015 | 0.69 ± 0.12 | 0.0013 | 1.12 ± 0.58 | 0.0016 |
| miR-135a* | 20.81 ± 5.62 | 1.17 ± 0.26 | 0.0016 | 1.24 ± 0.24 | 0.0016 | 1.27 ± 0.25 | 0.0017 |
| miR-195 | 8.77 ± 1.09 | 1.34 ± 0.43 | 8.9E−08 | 1.62 ± 0.42 | 2.0E−07 | 1.25 ± 0.37 | 7.0E−08 |
| miR-21 | 8.76 ± 1.81 | 1.24 ± 0.11 | 2.0E−04 | 1.74 ± 0.45 | 5.1E−04 | 3.35 ± 1.00 | 0.014 |
| miR-93 | 8.47 ± 1.53 | 1.56 ± 0.62 | 1.3E−04 | 2.68 ± 0.62 | 0.0027 | 3.34 ± 1.36 | 0.0255 |
| miR-486-5p | 7.85 ± 1.07 | 1.54 ± 0.51 | 2.9E−06 | 3.35 ± 1.63 | 0.0396 | 2.75 ± 0.72 | 6.4E−04 |
| miR-20a | 7.22 ± 0.78 | 1.34 ± 0.46 | 7.7E−08 | 2.24 ± 0.87 | 5.3E−04 | 0.99 ± 0.33 | 8.4E−09 |
| miR-16-1 | 6.45 ± 0.76 | 1.63 ± 0.65 | 4.2E−05 | 1.84 ± 0.77 | 3.8E−04 | 2.72 ± 0.58 | 0.0012 |
| miR-106a | 6.43 ± 0.92 | 1.28 ± 0.37 | 4.7E−06 | 3.38 ± 1.37 | 0.0378 | 1.98 ± 0.99 | 0.0238 |
| miR-483-5p | 5.90 ± 1.39 | 1.18 ± 0.26 | 0.0039 | 0 | NA | 1.26 ± 0.15 | 0.0039 |
| miR-222 | 5.53 ± 0.86 | 1.21 ± 0.25 | 1.5E−05 | 1.12 ± 0.30 | 1.5E−05 | 1.48 ± 0.74 | 0.0031 |
| miR-15a | 3.03 ± 0.44 | 1.08 ± 0.16 | 2.3E−04 | 1.07 ± 0.18 | 3.3E−04 | 2.20 ± 0.72 | 0.367 |

†P-values were calculated by two-sided t-test for each group relative to B-CLL patients

TABLE 3

The expression of plasma and corresponding B cell miRNAs based on ZAP-70 status and disease severity.

| Sample | ZAP-70 status | BCLL Stage | let-7e | miR-106a | miR-1225-5p | miR-135a* | miR-148a | miR-150* | miR-15a | miR-16-1 | miR-181a | miR-185 | miR-195 | miR-198 | miR-20a | miR-21 |
|---|---|---|---|---|---|---|---|---|---|---|---|---|---|---|---|---|
| Normal Plasma | | | 7.86 | 12.50 | 6.57 | 11.09 | 8.60 | 5.16 | 6.90 | 16.44 | 5.31 | 9.53 | 9.09 | 5.13 | 12.11 | 12.99 |
| B CLL Plasma | − | 0 | 9.72 | 15.36 | 7.27 | 14.99 | 8.77 | 8.44 | 8.66 | 19.29 | 5.72 | 12.34 | 12.46 | 5.45 | 15.20 | 15.76 |
| B CLL Plasma | − | I-II | 9.63 | 14.97 | 7.28 | 14.38 | 8.76 | 8.86 | 8.20 | 18.68 | 5.72 | 11.78 | 12.35 | 5.61 | 15.03 | 15.92 |
| B CLL Plasma | − | III-IV | 9.62 | 14.52 | 7.51 | 15.92 | 9.90 | 9.47 | 8.03 | 18.61 | 5.14 | 10.96 | 11.64 | 6.76 | 14.63 | 16.65 |
| B CLL Plasma | + | 0 | 9.09 | 13.73 | 7.48 | 11.56 | 8.53 | 5.61 | 6.64 | 18.28 | 5.05 | 10.53 | 11.09 | 4.80 | 13.50 | 13.67 |
| B CLL Plasma | + | II | 8.98 | 14.04 | 6.37 | 12.00 | 8.96 | 5.58 | 6.73 | 18.01 | 5.63 | 11.14 | 11.17 | 4.83 | 13.59 | 13.69 |
| B CLL Plasma | + | III | 9.07 | 14.72 | 7.32 | 10.98 | 8.72 | 6.28 | 7.55 | 17.47 | 6.05 | 10.53 | 11.53 | 5.64 | 14.41 | 14.11 |
| Normal Cell | | | 20.56 | 20.14 | 6.57 | 13.26 | 16.02 | 16.01 | 17.95 | 23.21 | 18.01 | 16.10 | 15.65 | 5.32 | 19.45 | 22.56 |
| B CLL Cell | − | 0 | 20.32 | 19.40 | 9.17 | 12.96 | 15.89 | 16.31 | 16.63 | 22.59 | 15.89 | 14.68 | 16.46 | 6.42 | 18.99 | 21.51 |
| B CLL Cell | − | I-II | 20.23 | 19.67 | 7.97 | 12.13 | 16.53 | 16.28 | 17.01 | 22.83 | 13.79 | 13.95 | 16.69 | 5.47 | 19.45 | 22.10 |
| B CLL Cell | − | III-IV | 20.14 | 19.64 | 7.60 | 12.38 | 16.62 | 16.10 | 17.36 | 23.10 | 12.46 | 13.87 | 16.68 | 4.80 | 19.47 | 22.36 |
| B CLL Cell | + | 0 | 21.18 | 20.42 | 9.43 | 15.98 | 15.89 | 18.08 | 23.61 | 16.68 | 16.05 | 16.66 | 6.46 | 20.03 | 22.72 | |
| B CLL Cell | + | II | 20.74 | 20.31 | 8.91 | 12.56 | 16.87 | 15.70 | 18.06 | 23.38 | 16.77 | 16.18 | 16.68 | 6.26 | 19.85 | 22.73 |
| B CLL Cell | + | III | 20.40 | 20.08 | 8.46 | 12.41 | 16.16 | 15.91 | 17.65 | 23.24 | 15.63 | 15.44 | 16.27 | 5.99 | 19.74 | 22.65 |

| Sample | ZAP-70 status | BCLL Stage | miR-221 | miR-222 | miR-23b | miR-29a | miR-331-5p | miR-34a | miR-451 | miR-483-5p | miR-486-5p | miR-625 | miR-638 | miR-93 | miR-939 |
|---|---|---|---|---|---|---|---|---|---|---|---|---|---|---|---|
| Normal Plasma | | | 7.45 | 9.56 | 5.94 | 11.20 | 5.47 | 7.47 | 15.74 | 5.58 | 13.45 | 5.17 | 7.16 | 10.77 | 5.49 |
| B CLL Plasma | − | 0 | 9.74 | 11.22 | 5.58 | 15.30 | 5.85 | 7.06 | 18.02 | 7.51 | 16.79 | 5.67 | 7.80 | 13.95 | 7.21 |
| B CLL Plasma | − | I-II | 9.60 | 11.35 | 5.60 | 15.63 | 5.55 | 7.48 | 16.82 | 7.95 | 15.99 | 5.77 | 7.84 | 13.50 | 8.34 |
| B CLL Plasma | − | III-IV | 8.88 | 11.39 | 5.14 | 16.05 | 5.98 | 6.85 | 16.37 | 8.18 | 15.31 | 6.08 | 8.38 | 12.77 | 8.69 |
| B CLL Plasma | + | 0 | 8.08 | 10.98 | 5.47 | 12.39 | 5.67 | 6.90 | 16.25 | 5.85 | 15.30 | 4.83 | 7.38 | 12.27 | 6.82 |
| B CLL Plasma | + | II | 8.70 | 10.81 | 5.06 | 12.44 | 5.43 | 6.68 | 16.68 | 5.48 | 15.24 | 5.04 | 6.94 | 12.86 | 6.12 |
| B CLL Plasma | + | III | 9.32 | 12.00 | 6.14 | 12.57 | 6.01 | 8.22 | 16.28 | 6.53 | 16.06 | 5.91 | 7.67 | 13.63 | 7.26 |
| Normal Cell | | | 18.46 | 19.26 | 12.45 | 21.91 | 11.02 | 13.33 | 11.98 | 9.87 | 14.24 | 12.03 | 8.27 | 19.89 | 13.37 |
| B CLL Cell | − | 0 | 16.78 | 18.34 | 10.92 | 21.98 | 12.18 | 14.43 | 9.88 | 11.08 | 14.95 | 11.65 | 10.31 | 18.67 | 15.92 |
| B CLL Cell | − | I-II | 15.42 | 18.12 | 9.80 | 22.45 | 11.32 | 15.46 | 9.74 | 9.34 | 14.95 | 11.30 | 9.16 | 18.32 | 15.16 |
| B CLL Cell | − | III-IV | 15.88 | 18.18 | 10.99 | 22.29 | 10.77 | 15.62 | 9.96 | 9.45 | 14.75 | 11.50 | 9.18 | 18.55 | 14.11 |
| B CLL Cell | + | 0 | 17.96 | 18.61 | 11.81 | 22.54 | 12.42 | 15.33 | 10.96 | 11.08 | 14.96 | 12.13 | 10.40 | 19.83 | 16.55 |
| B CLL Cell | + | II | 18.27 | 19.01 | 13.26 | 21.97 | 12.39 | 15.66 | 9.55 | 10.01 | 15.08 | 11.92 | 10.45 | 19.99 | 15.41 |
| B CLL Cell | + | III | 17.48 | 18.85 | 11.72 | 21.83 | 11.43 | 15.13 | 12.33 | 9.59 | 15.23 | 12.03 | 9.79 | 19.52 | 15.06 |

TABLE 4

Characteristics of the CLL patients

| Characteristic of CLL patients (N = 41) | Value |
|---|---|
| Sex | |
| Male - No. of patients (%) | 18 (44) |
| Female - No. of patients (%) | 23 (56) |
| Age | |
| Mean | 68 |
| Median | 71 |
| Range | 45-83 |
| Stage of the disease (Rai classification) | |
| 0 - No. of patients | 13 |
| I - No. of patients | 7 |
| II - No. of patients | 5 |
| III - No. of patients | 9 |
| IV - No. of patients | 7 |
| ZAP-70 expression (39 patients tested) | |
| Negative - No. of patients | 22/39 |
| Positive - No. of patients | 17/39 |
| CD38 expression (31 patients tested) | |
| Negative - No. of patients | 14/31 |
| Positive - No. of patients | 17/31 |
| IgV$_H$ mutational status (26 patients tested) | |
| Mutated - Homology <98% (%) | 18/26 (69) |
| Unmutated - Homology >98% (%) | 8/26 (31) |

TABLE 5

Differential expression of selected microRNAs in plasma of CLL patients and healthy donors

| miRNA | Plasma Fold Change BCLL compared to Normal | p-value | Correlation miRNA/ALC† |
|---|---|---|---|
| miR-195 | 6.54 | 8.8E−08 | 0.249 |
| miR-20a | 5.39 | 7.7E−08 | 0.309 |
| miR-106a | 5.02 | 4.7E−06 | 0.294 |
| miR-185 | 3.90 | 4.7E−06 | 0.078 |
| miR-486-5p | 5.00 | 2.9E−06 | 0.189 |
| miR-16-1 | 3.96 | 4.2E−05 | 0.182 |
| miR-222 | 4.57 | 1.5E−05 | −0.008 |
| miR-15a | 2.80 | 2.3E−04 | 0.386 |
| miR-21 | 7.06 | 1.9E−04 | 0.170 |
| miR-625 | 3.34 | 1.4E−04 | 0.387 |
| miR-93 | 5.43 | 1.3E−04 | 0.216 |
| let-7e | 2.70 | 0.0010 | −0.032 |
| miR-150 | 61.80 | 0.0011 | 0.617 |
| miR-29a | 22.68 | 0.0015 | 0.632 |
| miR-135a* | 17.78 | 0.0016 | 0.234 |
| miR-181a | 1.79 | 0.0020 | −0.141 |
| miR-150* | 29.07 | 0.0023 | 0.542 |
| miR-483-5p | 5.00 | 0.0039 | 0.507 |
| miR-1225-5p | 1.78 | 0.0064 | 0.302 |
| miR-451 | 3.05 | 0.010 | 0.166 |
| miR-221 | 4.51 | 0.021 | −0.144 |
| miR-23b | 0.65 | 0.249 | 0.154 |
| miR-34a | 1.38 | 0.312 | 0.229 |

†Pearson coefficient r computing the correlation between the plasma miRNA expression and the blood absolute lymphocyte count (ALC).

TABLE 6

Confirmed and predicted targets of candidate miRNA biomarkers in CLL

| miRNA | Confirmed and predicted target genes† |
|---|---|
| miR-195 | BCL2, CCND1, CDK6, E2F3, WEE1 |
| miR-20a | AEN, BCL2, BMPR2, PPARA |
| miR-106a | E2F1, EIF5A2, IL-10, MCL1, STAT3 |
| miR-185 | BMF, EIF5A, PAK6 |
| miR-486-5p | CD40, PIM1, SP5, STK4 |
| miR-16-1 | BCL2, CCND1 |
| miR-222 | Bim, p27$^{Kip1}$, p57$^{Kip2}$, MMP1, SOD2 |
| miR-15a | BCL2, BCL2L2, CCND1 |
| miR-21 | BMPR2, PTEN, SPRY2, STAT3 |
| miR-93 | CCND2, STAT3, TP53INP1 |
| let-7e | IL-10, PPARA, WIPI2 |
| miR-29a | B7-H3, CD26, DNMT3, PIK3R1, TCL1 |
| miR-135a* | IL-11RA, IL-24 |
| miR-181a | DUSP6, p27$^{Kip1}$, PLAG1, PTPN22, SHP-2, TCL1 |
| miR-150* | ITGB4BP, STK10 |
| miR-483-5p | ELK1, ERK1 (MAPK3) |
| miR-1225-5p | SEPT11, TALI, UVRAG |
| miR-451 | CDKN2D, MIF |
| miR-221 | Bim, c-kit, p27$^{Kip1}$, p57$^{Kip2}$ |
| miR-23b | GLS, c-MET, PLAU |
| miR-34a | BCL2, c-MET, WNT1 |

†Targets were extracted from literature or predicted with TargetScan 5.1, miRDB, and Microcosm tools.

REFERENCES

1. Kay, N. E. and T. D. Shanafelt, *Prognostic factors in chronic lymphocytic leukemia*. Curr Hematol Malig Rep, 2007. 2(1): p. 49-55.
2. Rai, K. R., et al., *Clinical staging of chronic lymphocytic leukemia*. Blood, 1975. 46(2): p. 219-34.
3. Binet, J. L., et al., Investigation of a new parameter in chronic lymphocytic leukemia: the percentage of large peripheral lymphocytes determined by the Hemalog D. Prognostic significance. Am J Med, 1977. 63(5): p. 683-8.
4. McManus, M. T., *MicroRNAs and cancer*. Semin Cancer Biol, 2003. 13(4): p. 253-8.
5. Klein, U., et al., The DLEU2/miR-15a/16-1 cluster controls B cell proliferation and its deletion leads to chronic lymphocytic leukemia. Cancer Cell, 2010. 17(1): p. 28-40.
6. Calin, G. A., et al., A MicroRNA signature associated with prognosis and progression in chronic lymphocytic leukemia. N Engl J Med, 2005. 353(17): p. 1793-801.
7. Haferlach, C., et al., Comprehensive genetic characterization of CLL: a study on 506 cases analysed with chromosome banding analysis, interphase FISH, IgV(H) status and immunophenotyping. Leukemia, 2007. 21(12): p. 2442-51.
8. Stamatopoulos, B., et al., MicroRNA-29c and microRNA-223 downregulation has in vivo significance in chronic lymphocytic leukemia and improves disease risk stratification. Blood, 2009.
9. Tsujiura, M., et al., Circulating microRNAs in plasma of patients with gastric cancers. Br J Cancer, 2010. 102(7): p. 1174-9.
10. Wang, K., et al., *Circulating microRNAs, potential biomarkers for drug-induced liver injury*. Proc Natl Acad Sci USA, 2009. 106(11): p. 4402-7.
11. Stamatopoulos, B., et al., Quantification of ZAP-70 mRNA in B cells by real-time PCR is a powerful prognostic factor in chronic lymphocytic leukemia. Clin Chem, 2007. 53(10): p. 1757-66.
12. Fulci, V., et al., Quantitative technologies establish a novel microRNA profile of chronic lymphocytic leukemia. Blood, 2007. 109(11): p. 4944-51.

13. Pallasch, C. P., et al., miRNA deregulation by epigenetic silencing disrupts suppression of the oncogene PLAG1 in chronic lymphocytic leukemia. Blood, 2009. 114(15): p. 3255-64.
14. Bichi, R., et al., Human chronic lymphocytic leukemia modeled in mouse by targeted TCL1 expression. Proc Natl Acad Sci USA, 2002. 99(10): p. 6955-60.
15. Cimmino, A., et al., *miR-15 and miR-16 induce apoptosis by targeting BCL2*. Proc Natl Acad Sci USA, 2005. 102 (39): p. 13944-9.
16. Kitada, S., et al., Expression of apoptosis-regulating proteins in chronic lymphocytic leukemia: correlations with In vitro and In vivo chemoresponses. Blood, 1998. 91(9): p. 3379-89.
17. Vrhovac, R., et al., Prognostic significance of the cell cycle inhibitor p27Kip1 in chronic B-cell lymphocytic leukemia. Blood, 1998. 91(12): p. 4694-700.
18. Cuesta, R., A. Martinez-Sanchez, and F. Gebauer, *miR-181a regulates cap-dependent translation of p27(kip1) mRNA in myeloid cells*. Mol Cell Biol, 2009. 29(10): p. 2841-51.
19. Galardi, S., et al., miR-221 and miR-222 expression affects the proliferation potential of human prostate carcinoma cell lines by targeting p27Kip1. J Biol Chem, 2007. 282(32): p. 23716-24.
20. de Totero, D., et al., The opposite effects of IL-15 and IL-21 on CLL B cells correlate with differential activation of the JAK/STAT and ERK1/2 pathways. Blood, 2008. 111(2): p. 517-24.
21. Redondo-Munoz, J., et al., Matrix metalloproteinase-9 is up-regulated by CCL21/CCR7 interaction via extracellular signal-regulated kinase-1/2 signaling and is involved in CCL21-driven B-cell chronic lymphocytic leukemia cell invasion and migration. Blood, 2008. 111(1): p. 383-6.

The invention claimed is:

1. A method to treat CLL in a subject which method comprises effecting a diminution of expression of NR6A1 in said subject.

2. The method of claim 1 wherein said diminution is effected by administering a composition that modulates the level of miR-23 and/or miR-181a in said subject.

3. The method of claim 1 wherein said diminution is effected by administering an antisense oligonucleotide directed to mRNA encoding NR6A1.

4. The method of claim 1 wherein said diminution is effected by administering a composition that comprises siRNA directed to NR6A1 gene expression.

* * * * *